United States Patent
Kim et al.

(10) Patent No.: US 9,829,695 B2
(45) Date of Patent: Nov. 28, 2017

(54) ARRAY LEVEL FOURIER PTYCHOGRAPHIC IMAGING

(71) Applicant: California Institute of Technology, Pasadena, CA (US)

(72) Inventors: Jinho Kim, Pasadena, CA (US); Changhuei Yang, Alhambra, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/007,196

(22) Filed: Jan. 26, 2016

(65) Prior Publication Data
US 2016/0216503 A1  Jul. 28, 2016

Related U.S. Application Data

(60) Provisional application No. 62/107,628, filed on Jan. 26, 2015, provisional application No. 62/107,631, filed on Jan. 26, 2015.

(51) Int. Cl.
*G02B 21/36* (2006.01)
*G02B 21/16* (2006.01)
(Continued)

(52) U.S. Cl.
CPC ....... *G02B 21/365* (2013.01); *G01N 21/6452* (2013.01); *G01N 21/6456* (2013.01);
(Continued)

(58) Field of Classification Search
CPC . G01B 9/02; G01B 11/02; G06K 9/20; G02B 5/203; G02B 21/361; G02B 21/365
See application file for complete search history.

(56) References Cited

U.S. PATENT DOCUMENTS 6,144,365 A  11/2000 Young et al.
6,154,196 A  11/2000 Fleck et al.
(Continued)

FOREIGN PATENT DOCUMENTS

JP  2007-299604 A  11/2007
JP  2010-012222 A   1/2010
(Continued)

OTHER PUBLICATIONS

U.S. Appl. No. 15/007,159, filed Jan. 26, 2016 entitled "Multi-well Fourier Ptychographic and Fluorescence Imaging".
(Continued)

*Primary Examiner* — David Porta
*Assistant Examiner* — Faye Boosalis
(74) *Attorney, Agent, or Firm* — Sheila Martinez-Lemke; Weaver Austin Villeneuve & Sampson LLP

(57) ABSTRACT

In one aspect an imaging system includes: an illumination system including an array of light sources; an optical system including one or more lens arrays, each of the lens arrays including an array of lenses, each of the lenses in each of the one or more lens arrays in alignment with a corresponding set of light sources of the array of light sources; an imaging system including an array of image sensors, each of the image sensors in alignment with a corresponding lens or set of lenses of the one or more lens arrays, each of the image sensors configured to acquire image data based on the light received from the corresponding lens or set of lenses; a plate receiver system capable of receiving a multi-well plate including an array of wells, the plate receiver system configured to align each of the wells with a corresponding one of the image sensors; and a controller configured to control the illumination of the light sources and the acquisition of image data by the image sensors, the controller further configured to perform: an image acquisition process includ-
(Continued)

ing a plurality of scans, each scan associated with a unique pattern of illumination, each of the image sensors configured to generate an image for a respective one of the wells during each scan; and an image reconstruction process during which the controller performs a fourier ptychographic operation to generate a reconstructed image for each of the wells based on the image data captured for the respective well during each of the scans.

20 Claims, 18 Drawing Sheets

(51) Int. Cl.
 G02B 21/00 (2006.01)
 G01N 21/64 (2006.01)
(52) U.S. Cl.
 CPC ..... *G01N 21/6458* (2013.01); *G02B 21/0076* (2013.01); *G02B 21/16* (2013.01); *G01N 2021/6478* (2013.01); *G01N 2201/0446* (2013.01)

(56) References Cited

U.S. PATENT DOCUMENTS

| | | | |
|---|---|---|---|
| 6,747,781 | B2 | 6/2004 | Trisnadi |
| 6,905,838 | B1 | 6/2005 | Bittner |
| 7,436,503 | B1 | 10/2008 | Chen et al. |
| 7,460,248 | B2 | 12/2008 | Kurtz et al. |
| 7,706,419 | B2 | 4/2010 | Wang et al. |
| 7,787,588 | B1 | 8/2010 | Yun et al. |
| 8,271,251 | B2 | 9/2012 | Schwartz et al. |
| 8,271,521 | B2 | 9/2012 | Vadon et al. |
| 8,313,031 | B2 | 11/2012 | Vinogradov |
| 8,497,934 | B2 | 7/2013 | Milnes et al. |
| 8,624,968 | B1 | 1/2014 | Hersee et al. |
| 8,942,449 | B2 | 1/2015 | Maiden |
| 9,029,745 | B2 | 5/2015 | Maiden |
| 9,426,455 | B2 | 8/2016 | Horstmeyer et al. |
| 9,497,379 | B2 | 11/2016 | Ou et al. |
| 2001/0055062 | A1 | 12/2001 | Shioda et al. |
| 2002/0141051 | A1 | 10/2002 | Vogt et al. |
| 2003/0116436 | A1 | 6/2003 | Amirkhanian et al. |
| 2004/0146196 | A1 | 7/2004 | Van Heel |
| 2004/0190762 | A1 | 9/2004 | Dowski, Jr. et al. |
| 2006/0173313 | A1 | 8/2006 | Liu et al. |
| 2006/0291707 | A1 | 12/2006 | Kothapalli et al. |
| 2007/0057184 | A1 | 3/2007 | Uto et al. |
| 2007/0133113 | A1 | 6/2007 | Minabe et al. |
| 2007/0159639 | A1 | 7/2007 | Teramura et al. |
| 2007/0171430 | A1 | 7/2007 | Tearney et al. |
| 2007/0189436 | A1 | 8/2007 | Goto et al. |
| 2008/0101664 | A1 | 5/2008 | Perez |
| 2009/0046164 | A1 | 2/2009 | Shroff et al. |
| 2009/0079987 | A1 | 3/2009 | Ben-Ezra et al. |
| 2009/0125242 | A1 | 5/2009 | Choi et al. |
| 2009/0284831 | A1 | 11/2009 | Schuster et al. |
| 2009/0316141 | A1 | 12/2009 | Feldkhun |
| 2010/0135547 | A1 | 6/2010 | Lee et al. |
| 2010/0271705 | A1 | 10/2010 | Hung |
| 2011/0075928 | A1 | 3/2011 | Jeong et al. |
| 2011/0192976 | A1 | 8/2011 | Own et al. |
| 2011/0235863 | A1 | 9/2011 | Maiden |
| 2012/0069344 | A1 | 3/2012 | Liu |
| 2012/0099803 | A1 | 4/2012 | Ozcan et al. |
| 2012/0105618 | A1 | 5/2012 | Brueck et al. |
| 2012/0118967 | A1 | 5/2012 | Gerst |
| 2012/0157160 | A1 | 6/2012 | Ozcan et al. |
| 2012/0218379 | A1 | 8/2012 | Ozcan et al. |
| 2012/0248292 | A1 | 10/2012 | Ozcan et al. |
| 2012/0250032 | A1 | 10/2012 | Wilde et al. |
| 2012/0281929 | A1 | 11/2012 | Brand et al. |
| 2013/0083886 | A1 | 4/2013 | Carmi et al. |
| 2013/0093871 | A1 | 4/2013 | Nowatzyk et al. |
| 2013/0094077 | A1 | 4/2013 | Brueck et al. |
| 2013/0100525 | A1 | 4/2013 | Chiang et al. |
| 2013/0170767 | A1 | 7/2013 | Choudhury et al. |
| 2013/0182096 | A1 | 7/2013 | Boccara et al. |
| 2013/0223685 | A1 | 8/2013 | Maiden |
| 2014/0007307 | A1 | 1/2014 | Routh, Jr. et al. |
| 2014/0029824 | A1 | 1/2014 | Shi et al. |
| 2014/0043616 | A1 | 2/2014 | Maiden et al. |
| 2014/0050382 | A1 | 2/2014 | Adie et al. |
| 2014/0118529 | A1 | 5/2014 | Zheng et al. |
| 2014/0126691 | A1 | 5/2014 | Zheng et al. |
| 2014/0152801 | A1 | 6/2014 | Fine et al. |
| 2014/0153692 | A1 | 6/2014 | Larkin et al. |
| 2014/0160236 | A1 | 6/2014 | Ozcan et al. |
| 2014/0267674 | A1 | 9/2014 | Mertz et al. |
| 2014/0347672 | A1 | 11/2014 | Pavillon et al. |
| 2014/0368812 | A1 | 12/2014 | Humphry et al. |
| 2015/0036038 | A1 | 2/2015 | Horstmeyer et al. |
| 2015/0054979 | A1 | 2/2015 | Ou et al. |
| 2015/0160450 | A1 | 6/2015 | Ou et al. |
| 2015/0264250 | A1 | 9/2015 | Ou et al. |
| 2015/0331228 | A1 | 11/2015 | Horstmeyer et al. |
| 2016/0088205 | A1 | 3/2016 | Horstmeyer et al. |
| 2016/0178883 | A1 | 6/2016 | Horstmeyer et al. |
| 2016/0210763 | A1 | 7/2016 | Horstmeyer et al. |
| 2016/0216208 | A1 | 7/2016 | Kim et al. |
| 2016/0266366 | A1 | 9/2016 | Chung et al. |
| 2016/0320595 | A1 | 11/2016 | Horstmeyer et al. |
| 2016/0320605 | A1 | 11/2016 | Ou et al. |
| 2016/0341945 | A1 | 11/2016 | Ou et al. |

FOREIGN PATENT DOCUMENTS

| | | |
|---|---|---|
| KR | 10-1998-0075050 A | 11/1998 |
| WO | WO 99/53469 A1 | 10/1999 |
| WO | WO 2002/102128 A1 | 12/2002 |
| WO | 2003/062744 A1 | 7/2003 |
| WO | WO 2008/116070 A1 | 9/2008 |
| WO | WO 2011/093043 A1 | 8/2011 |
| WO | WO 2012/037182 A1 | 3/2012 |
| WO | WO 2014/070656 A1 | 5/2014 |
| WO | 2015/017730 A1 | 2/2015 |
| WO | 2015/027188 A1 | 2/2015 |
| WO | 2016/090331 | 6/2016 |
| WO | 2016/106379 A1 | 6/2016 |
| WO | 2016/118761 A1 | 7/2016 |
| WO | 2016/123156 A1 | 8/2016 |
| WO | 2016/123157 A1 | 8/2016 |
| WO | 2016/149120 A1 | 9/2016 |
| WO | WO 2016/187591 A1 | 11/2016 |
| WO | WO 2017081539 A1 | 5/2017 |
| WO | WO 2017081540 A1 | 5/2017 |
| WO | WO 2017081542 A2 | 5/2017 |

OTHER PUBLICATIONS

U.S. Appl. No. 14/979,154, filed Dec. 22, 2015 entitled "EPI-Illumination Fourier Ptychographic Imaging for Thick Samples".
U.S. Appl. No. 15/003,559, filed Jan. 21, 2016 entitled "Fourier Ptychographic Tomography".
U.S. Appl. No. 15/068,389, filed Mar. 11, 2016 entitled "Correcting for Aberrations in Incoherent Imaging Systems Using Fourier Ptychographic Techniques".
U.S. Appl. No. 15/081,659, filed Mar. 25, 2016 entitled "Fourier Ptychographic Retinal Imaging Methods and Systems".
U.S. Office Action dated Oct. 5, 2015 in U.S. Appl. No. 14/065,305.
U.S. Notice of Allowance dated Dec. 4, 2015 in U.S. Appl. No. 14/065,305.
U.S. Notice of Allowance dated Jan. 14, 2016 in U.S. Appl. No. 14/448,850.
U.S. Notice of Allowance dated Jan. 22, 2016 in U.S. Appl. No. 14/466,481.
U.S. Notice of Allowance dated Apr. 13, 2016 in U.S. Appl. No. 14/448,850.
U.S. Notice of Allowance dated Apr. 22, 2016 in U.S. Appl. No. 14/466,481.

(56) References Cited

OTHER PUBLICATIONS

International Search Report and Written Opinion dated Feb. 21, 2014 in PCT/US2013/067068.
International Preliminary Report on Patentability dated May 14, 2015 in PCT/US2013/067068.
European Third-Party Observations, dated Dec. 14, 2015 in EP Application No. 13851670.3.
European Extended Search Report dated Mar. 31, 2016 in EP Application No. 13851670.3.
International Preliminary Report on Patentability dated Mar. 3, 2016 issued in PCT/US2014/052351.
International Search Report and Written Opinion dated Dec. 5, 2014 issued in PCT/US2014/052351.
International Search Report and Written Opinion dated Nov. 13, 2014 issued in PCT/US2014/049297.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
"About Molemap," Retrieved Oct. 23, 2015, 2 pages. [http://molemap.net.au/about-us/].
Abramomwitz, M. et al, "Immersion Media," Olympus Microscopy Resource Center, 2012, 6 pp. [http://www.olympusmicro.com/primer/anatomy/immersion.html].
Abramomwitz, M., et al, "Field Curvature," Olympus Microscopy Resource Center, 2012, 3 pp. [http://www.olympusmicro.com/primer/anatomy/fieldcurvature.html].
"Age-Related Macular Degeneration (AMD) | National Eye Institute." [Online]. Available: https://www.nei.nih.gov/eyedata/amd#top. [Accessed: Apr. 5, 2016].
Alexandrov, S., et al, "Spatial information transmission beyond a system's diffraction limit using optical spectral encoding of the spatial frequency," Journal of Optics A: Pure and Applied Optics 10, 025304 (2008).
Alexandrov, S.A., et al, "Synthetic Aperture Fourier holographic optical microscopy," Phys. Rev. Lett. 97, 168102 (2006).
Arimoto, H., et al, "Integral three-dimensional imaging with digital reconstruction," Opt. Lett. 26, 157-159 (2001).
Balan, R., et al, "On signal reconstruction without phase, Applied and Computational Harmonic Analysis 20," No. 3 (2006): 345-356.
Balan, R., et al, "Painless reconstruction from magnitudes of frame coefficients," J Fourier Anal Appl 15:488-501 (2009).
Bauschke, H.H., et al, "Phase retrieval, error reduction algorithm, and Fienup variants: a view from convex optimization," J Opt Soc Am A 19:1334-1345 (2002).
Becker, S., et al, "Templates for convex cone problems with applications to sparse signal recovery," Technical report, Department of Statistics, Stanford University, (2010), 48 Pages.
Betti, R., et al, "Observational study on the mitotic rate and other prognostic factors in cutaneous primary melanoma arising from naevi and from melanoma de novo," Journal of the European Academy of Dermatology and Venereology, 2014.
Bian, L., et al, "Fourier ptychographic reconstruction using Wirtinger flow optimization," Opt. Express 23:4856-4866 (2015).
Bian, Z., et al, "Adaptive system correction for robust Fourier ptychographic imaging," Optics express, 2013. 21(26): p. 32400-32410.
BioTek® Brochure: BioTek's Multi-Mode Microplate Reading Techonologies, 2016, 2 pp. [http://www.biotek.com].
Bishara, W., et al, "Holographic pixel super-resolution in portable lensless on-chip microscopy using a fiber-optic array," Lab Chip 11(7), 1276-1279 (2011).
Bishara, W., et al, "Lensfree on-chip microscopy over a wide field-of-view using pixel super-resolution," Opt. Express 18(11), 11181-11191 (2010).
Blum, A., et al, "Clear differences in hand-held dermoscopes," JDDG: Journal der Deutschen Dermatologischen Gesellschaft, 2006, 4(12): p. 1054-1057.
Blum, A., et al, Dermatoskopie von Hauttumoren: Auflichtmikroskopie; Dermoskopie; digitale Bildanalyse; mit 28 Tabellen. 2003: Springer DE, Chapter 4 "Dermatoskopisch sichtbare Strukturen" p. 15-66.
Born, M., et al, "Principles of Optics: Electromagnetic theory of propagation, interference and diffraction of light" 7th Ed., Cambridge Univ. Press, (1999) pp. 1-31.
Brady, D., et al, "Multiscale gigapixel photography," Nature 486, 386-389 (2012).
Burer, S., et al, "A nonlinear programming algorithm for solving semidefinite programs via low-rank factorization," Math Program, Ser B 95:329-357 (2003).
Burer, S., et al, "Local minima and convergence in low-rank semidefinite programming. Math Program," Ser A 103:427-444 (2005).
Candes, E.J., et al, "Phase retrieval via matrix completion," SIAM J. Imaging Sci. 6:199-225 (2012).
Candes, E.J., et al, "Phase retrieval via Wirtinger flow: theory and algorithms," IEEE Trans. Info. Theory 61:1985-2007 (2015).
Candes, E.J., et al, "PhaseLift: exact and stable signal recovery from magnitude measurements via convex programming.," Comm Pure Appl Math 66:1241-1274 (2013).
Carroll, J., "Adaptive optics retinal imaging: applications for studying retinal degeneration," Arch. Ophthalmol., vol. 126, pp. 857-858, 2008.
Chao, W. et al, "Soft X-ray microscopy at a spatial resolution better than 15 nm," Nature Letters, vol. 435/30, Jun. 2005 pp. 1210-1213.
Chen, T., et al, "Polarization and phase shifting for 3D scanning of translucent objects," Proc. CVPR, (2007).
Chin, L., et al, "Malignant melanoma: genetics and therapeutics in the genomic era," Genes & development, 2006, 20(16): p. 2149-2182.
Choi, W., et al, "Tomographic phase microscopy," Nature Methods 4(9) (2007), pp. 1-3 Published Online Aug. 12, 2007.
Chung, J., et al, "Counting White Blood Cells from a Blood Smear Using Fourier Ptychographic Microscopy," PLoS One 10(7), e0133489 (2015).
Chung, J., et al, "Wide field-of-view fluorescence image deconvolution with aberration-estimation from Fourier ptychography," Feb. 1, 2016, vol. 7, No. 2, Biomedical Optics Express 352.
Colomb, T., et al, "Automatic procedure for aberration compensation in digital holographic microscopy and applications to specimen shape compensation," Appl. Opt. 45, 851-863 (2006).
De Sa, C., et al, "Global convergence of stochastic gradient descent for some non convex matrix problems," Proc. 32nd Int. Conf. Machine Learning (2015), 10 pp.
Debailleul, M., et al, "High-resolution three-dimensional tomographic diffractive microscopy of transparent inorganic and biological samples," Optic Letters 34 (2008).
Denis, L., et al, "Inline hologram reconstruction with sparsity constraints," Opt. Lett. 34, pp. 3475-3477 (2009).
Di, J., et al, "High resolution digital holographic microscopy with a wide field of view based on a synthetic aperture technique and use of linear CCD scanning," Appl. Opt. 47, pp. 5654-5659 (2008).
Dierolf, M., et al, "Ptychographic coherent diffractive imaging of weakly scattering specimens," New J. Phys. 12, 035017 (2010).
"Doctor Mole—Skin Cancer App," Retrieved Oct. 23, 2015, 1 page. [http://www.doctormole.com].
Dong, S., et al, "FPscope: a field-portable high-resolution microscope using a cellphone lens," Biomed. Opt. Express 5(10), 3305-3310 (2014).
Dong, S., et al, "High-resolution fluorescence imaging via pattern-illuminated Fourier ptychography," Opt. Express 22(17), 20856-20870 (2014).
Dong, S., et al, "Aperture-scanning Fourier ptychography for 3D refocusing and super-resolution macroscopic imaging," pp. 13586-13599 (Jun. 2, 2014).
Eldar, Y.C., et al, "Sparse phase retrieval from short-time Fourier measurements," IEEE Signal Processing Letters 22, No. 5 (2015): 638-642.
Emile, O., et al, "Rotating polarization imaging in turbid media," Optics Letters 21(20), (1996).

(56) References Cited

OTHER PUBLICATIONS

Faulkner, H.M.L., and Rodenburg, J.M., "Error tolerance of an iterative phase retrieval algorithm for moveable illumination microscopy," Ultramicroscopy 103(2), 153-164 (2005).
Faulkner, H.M.L., and Rodenburg, J.M., "Movable aperture lensless transmission microscopy: a novel phase retrieval algorithm," Phys. Rev. Lett. 93, 023903 (2004).
Fazel, M., "Matrix rank minimization with applications," PhD Thesis (Stanford University, Palo Alto, CA). (2002).
Feng, P., et al, "Long-working-distance synthetic aperture Fresnel off-axis digital holography," Optics Express 17, pp. 5473-5480 (2009).
Fienup, J. R., "Invariant error metrics for image reconstruction," Appl. Opt. 36(32), 8352-8357 (1997).
Fienup, J. R., "Lensless coherent imaging by phase retrieval with an illumination pattern constraint," Opt. Express 14, 498-508 (2006).
Fienup, J. R., "Phase retrieval algorithms: a comparison," Appl. Opt. 21, 2758-2769 (1982).
Fienup, J. R., "Reconstruction of a complex-valued object from the modulus of its Fourier transform using a support constraint," J. Opt. Soc. Am. A 4, 118-123 (1987).
Fienup, J. R., "Reconstruction of an object from the modulus of its Fourier transform," Opt. Lett. 3, 27-29 (1978).
Gan, X., et al, "Image enhancement through turbid media under a microscope by use of polarization gating methods," JOSA A 16(9), (1999).
Gerke T.D., et al, "Aperiodic volume optics," Nature Photonics (2010), vol. 4, pp. 188-193.
Ghosh, A., et al, "Multiview face capture using polarized spherical gradient illumination," ACM Transactions on Graphics 30(6) (2011).
Godara, P., et al, "Adaptive optics retinal imaging: emerging clinical applications.," Optom. Vis. Sci., vol. 87, No. 12, pp. 930-941, Dec. 2010.
Goodman, J.W., "Introduction to Fourier Optics," Roberts & Company Publication, Third Edition, chapters 1-6, pp. 1-172 (2005).
Goodson, A.G., et al, "Comparative analysis of total body and dermatoscopic photographic monitoring of nevi in similar patient populations at risk for cutaneous melanoma," Dermatologic Surgery, 2010. 36(7): p. 1087-1098.
Granero, L., et al, "Synthetic aperture superresolved microscopy in digital lensless Fourier holography by time and angular multiplexing of the object information," Appl. Opt. 49, pp. 845-857 (2010).
Grant, M., et al, "CVX: Matlab software for disciplined convex programming," version 2.0 beta. http://cvxr.com/cvx, (Sep. 2013), 3 pages.
Greenbaum, A., et al, "Field-portable wide-field microscopy of dense samples using multi-height pixel super resolution based lensfree imaging," Lab Chip 12(7), 1242-1245 (2012).
Greenbaum, A., et al, "Increased space—bandwidth product in pixel super-resolved lensfree on-chip microscopy," Sci. Rep. 3, p. 1717 (2013).
Gruev, V., et al, "Dual-tier thin film polymer polarization imaging sensor," Optics Express, vol. 18, No. 18, 12 pages. (2010).
Guizar-Sicairos, M., and Fienup, J.R.,"Phase retrieval with transverse translation diversity: a nonlinear optimization approach," Opt. Express 16, 7264-7278 (2008).
Gunturk, B.K., et al, "Image Restoration: Fundamentals and Advances," vol. 7, Chapter 3, pp. 63-68 (CRC Press, 2012).
Gustafsson, M.G.L., "Surpassing the lateral resolution limit by a factor of two using structured illumination microscopy," J. Microsc. 198, 82-87 (2000).
Gutzler, T., et al, "Coherent aperture-synthesis, wide-field, high-resolution holographic microscopy of biological tissue," Opt. Lett. 35, pp. 1136-1138 (2010).
Haigh, S. J., et al, (2009) "Atomic structure imaging beyond conventional resolution limits in the transmission electron microscope"; Physical Review Letters 103. 126101-1 126101-4, Sep. 18, 2009.

Han, C., et al, "Wide Field-of-View On-Chip Talbot Fluorescence Microscopy for Longitudinal Cell Culture Monitoring from within the Incubator" Anal. Chem. 85(4), 2356-2360 (2013).
Hillman, T.R., et al, "High-resolution, wide-field object reconstruction with synthetic aperture Fourier holographic optical microscopy," Opt. Express 17, pp. 7873-7892 (2009).
Hofer, H., et al, "Dynamics of the eye's wave aberration," J. Opt. Soc. Am. A, vol. 18, No. 3, p. 497, 2001.
Hofer, H., et al, "Organization of the human trichromatic cone mosaic.," J. Neurosci., vol. 25, No. 42, pp. 9669-9679, Oct. 2005.
Hong, S-H., et al, "Three-dimensional volumetric object reconstruction using computational integral imaging," Opt. Express 12, 483-491 (2004).
Hoppe, W., "Diffraction in inhomogeneous primary wave fields. 1. Principle of phase determination from electron diffraction interference," Acta Crystallogr. A25, 495-501 1969.
Horstmeyer, R., et al, "A phase space model of Fourier ptychographic microscopy," Optics Express, 2014. 22(1): p. 338-358.
Horstmeyer, R., et al, "Digital pathology with fourier ptychography," Comput. Med. Imaging Graphics 42, 38-43 (2015).
Horstmeyer, R., et al, "Overlapped fourier coding for optical aberration removal," Manuscript in preparation, 19 pages. (2014).
Horstmeyer, R., et al, "Solving ptychography with a convex relaxation," Physics Optics (2014) 1-8 pages.
Hüe, F. et al, "Wave-front phase retrieval in transmission electron microscopy via ptychography," Phys. Rev. B 82, 121415 (2010).
Humphry, M., et al, "Ptychographic electron microscopy using high-angle dark-field scattering for sub-nanometre resolution imaging," Nat. Commun. 3, 730 (2012).
IncuCyte® ZOOM System, Brochure, 1-4 pp. (2016) (retrieved Feb. 25, 2016), [http://www.essenbioscience.com/media/uploads/files/8000-0333-E00-IncuCyte_ZOOM_brochure.pdf].
Jaganathan, K., et al, "Recovery of sparse 1-D signals from the magnitudes of their Fourier transform," IEEE International Symposium on Information Theory Proceedings (2012): 1473-1477.
Jaganathan, K., et al, "Phase retrieval with masks using convex optimization," IEEE International Symposium on Information Theory Proceedings (2015): 1655-1659.
Jaganathan, K., et al, "STFT Phase retrieval: uniqueness guarantees and recovery algorithms," arXiv preprint arXiv:1508.02820 (2015).
Joeres, S., et al, "Retinal imaging with adaptive optics scanning laser ophthalmoscopy in unexplained central ring scotoma.," Arch. Ophthalmol., vol. 126, No. 4, pp. 543-547, Apr. 2008.
Jung, J.H., et al, "Microfluidic-integrated laser-controlled microactuators with on-chip microscopy imaging functionality," Lab Chip 14 (19), Oct. 7, 2014, pp. 3781-3789.
Kay, D. B., et al, "Outer retinal structure in best vitelliform macular dystrophy.," JAMA Ophthalmol., vol. 131, pp. 1207-1215, 2013.
Kim, J., et al, Incubator embedded cell culture imaging system (EmSight) based on Fourier ptychographic microscopy. EmSight manuscript, Optical Society of America, 2015.
Kim, M., et al, "High-speed synthetic aperture microscopy for live cell imaging," Opt. Lett. 36, pp. 148-150 (2011).
Kirkland, A.I., et al, "Multiple beam tilt microscopy for super resolved imaging;" Japanese Society of Electron Microscopy: Journal of Electron Microscopy I: 11-22(1997), vol. 46, No. 1 1997.
Kirkland, A.I., et al, "Super-resolution by aperture synthesis: tilt series reconstruction in CTEM," Ultramicroscopy 57, (1995) 355-374, Received May 27, 1994, in final form Oct. 2, 1994; 1995 Elsevier Science B.V. SSDI 0304-3991(94)00191-x.
Kittler, H., et al, "Morphologic changes of pigmented skin lesions: a useful extension of the ABCD rule for dermatoscopy," Journal of the American Academy of Dermatology, 1999. 40(4): p. 558-562.
Kozak, I., "Retinal imaging using adaptive optics technology.," Saudi J. Ophthalmol. Off. J. Saudi Ophthalmol. Soc., vol. 28, No. 2, pp. 117-122, Apr. 2014.
Lauer, V., "New Approach to optical diffraction tomography yielding a vector equation of diffraction tomography and a novel tomography microscope," Journal of Microscopy, vol. 205, Pt 2 Feb. 2002, pp. 165-176, The Royal Microscopical Society 2001.
Lee, K., et al, "Synthetic Fourier transform light scattering," Optics Express 21 (2013).

(56) References Cited

OTHER PUBLICATIONS

Levoy, M., et al, "Light field microscopy," ACM Trans. Graphics 25, (2006).
Levoy, M., et al, "Recording and controlling the 4D light field in a microscope using microlens arrays," J. Microsc. 235 (2009).
Li, X., et al, "Sparse signal recovery from quadratic measurements via convex programming," SIAM Journal on Mathematical Analysis 45, No. 5 (2013): 3019-3033.
Lohmann, A. W., et al, "Space—bandwidth product of optical signals and systems," J. Opt. Soc. Am. A 13, pp. 470-473 (1996).
Lue, N., et al, "Live Cell Refractometry Using Hilbert Phase Microscopy and Confocal Reflectance Microscopy," The Journal of Physical Chemistry A, 113, pp. 13327-13330 (2009).
LUXEXCEL® Brochure, LUXEXCEL: 3D Printing Service Description, Retrieved Mar. 7, 2016, 5 pp. [http://www.luxexcel.com].
"Lytro," Retrieved Oct. 23, 2015, 6 pp. [https://www.lytro.com/].
Ma, W., et al, "Rapid Acquisition of Specular and Diffuse Normal Maps from Polarized Spherical Gradient Illumination," University of Southern California, Institute for Creative Technologies, 12 pages. (2007).
Mahajan, V. N., "Zernike circle polynomials and optical aberrations of systems with circular pupils," Appl. Opt. 33(34), 8121-8124 (1994).
Maiden, A. M., et al, "A new method of high resolution, quantitative phase scanning microscopy," in: M.T. Postek, D.E. Newbury, S.F. Platek, D.C. Joy (Eds.), SPIE Proceedings of Scanning Microscopy, 7729, 2010.
Maiden, A. M., et al, "An improved ptychographical phase retrieval algorithm for diffractive imaging," Ultramicroscopy 109(10), 1256-1262 (2009).
Maiden, A. M., et al, "Superresolution imaging via ptychography," Journal of the Optical Society of America A. Apr. 2011, vol. 28 No. 4, pp. 604-612.
Maiden, A. M., et al, "Optical ptychography: a practical implementation with useful resolution," Opt. Lett. 35, 2585-2587 (2010).
Marchesini S., "A unified evaluation of iterative projection algorithms for phase retrieval," Rev Sci Instrum 78:011301 (2007).
Marchesini S., et al, "Augmented projections for ptychographic imaging," Inverse Probl 29:115009 (2013).
Marrison, J., et al, "Ptychography—a label free, high-contrast imaging technique for live cells using quantitative phase information," Sci. Rep. 3, 2369 (2013).
Medoff, B.P., et al, "Iterative convolution backprojection algorithms for image reconstruction from limited data," J. Opt. Soc. Am. vol. 73, No. 11, Nov. 1983, pp. 1493-1500.
"Melafind," Retrieved Oct. 23, 2015, 4 pages. [http://www.melafind.com/].
Meyer, R.R., et al, "A method for the determination of the wave aberration function of high-resolution TEM," Ultramicroscopy 99 (2004) 115-123: Elsevier B.V. Doi: 10.1016/j.ultramic.2003.11.001.
Miao, J., et al, "High Resolution 3D X-Ray Diffraction Microscopy," Physical Review Letters, Aug. 19, 2002, vol. 89, No. 8, pp. 1-4.
Mico, V., et al, "Synthetic aperture microscopy using off-axis illumination and polarization coding," Optics Communications, pp. 276, 209-217 (2007).
Mico, V., et al, "Synthetic aperture superresolution with multiple off-axis holograms," JOSA A 23, pp. 3162-3170 (2006).
Mir, M. et al, "Optical measurement of cycle-dependent cell growth," Proceedings of the National Academy of Sciences 108, pp. 13124-13129 (2011).
Mir, M., et al, "Blood screening using diffraction phase cytometry," Journal of Biomedical Optics 15, pp. 027016-027014 (2010).
Moreno, I., "Creating a desired lighting pattern with an LED array," 8th International Conference on Solid State Lighting, Proceedings of SPIE, vol. 7058, 2008, 9 pp.
Mrejen, S., et al, "Adaptive optics imaging of cone mosaic abnormalities in acute macular neuroretinopathy.," Ophthalmic Surg. Lasers Imaging Retina, vol. 45, No. 6, pp. 562-569, Jan. 2014.

Nayar, S. K., et al, "Fast separation of direct and global components of a scene using high frequency illumination," ACM Transactions on Graphics 25(3) (2006).
Ng, R., et al, "Light field photography with a hand-held plenoptic camera", Computer Science Technical Report CSTR, 2005. 2(11).
Nomura, H., and Sato, T., "Techniques for measuring aberrations in lenses used in photolithography with printed patterns," Appl. Opt. 38(13), 2800-2807 (1999).
Ohlsson, H., et al. "Compressive phase retrieval from squared output measurements via semidefinite programming," arXiv:1111.6323 (2011).
Ou, X., et al, "High numerical aperture Fourier ptychography: principle, implementation and characterization," Opt. Express 23:3472-3491 (2015).
Ou, X., et al, "Quantitative phase imaging via Fourier ptychographic microscopy," Optics Letters, 2013. 38(22): p. 4845-4848.
Ou, X., et al, "Embedded pupil function recovery for Fourier ptychographic microscopy," Optics Express 22 (5), pp. 4960-4972 (2014), with Erratum (2015).
Ou, X., et al, "Embedded pupil function recovery for Fourier ptychographic microscopy," submitted Dec. 26, 2013; 13 pp.
Pacheco, S., et al, "Reflective Fourier Ptychography," J. Biomed. Opt. 21(2), pp. 026010-1-026010-7, (Feb 18, 2016). [http://biomedicaloptics.spiedigitallibrary.org].
Recht, B., et al, "Guaranteed minimum-rank solutions of linear matrix equations via nuclear norm minimization," SIAM Review 52, No. 3 (2010): 471-501.
Reinhard, E., et al, "High Dynamic Range Imaging: Acquisition, Display, and Image-based Lighting" (Morgan Kaufmann, 2010).
Rodenburg, J. M., et al, "A phase retrieval algorithm for shifting illumination," Appl. Phys. Lett. 85, 4795-4797 (2004).
Rodenburg, J. M., et al, "Hard-X-ray lensless imaging of extended objects," Phys. Rev. Lett. 98, 034801 (2007).
Rodenburg, J. M., et al, "The theory of super-resolution electron microscopy via Wigner-distribution deconvolution," Phil. Trans. R. Soc. Lond. A 339, 521-553 (1992).
Rodenburg, J., "Ptychography and related diffractive imaging methods," Adv. Imaging Electron Phys.150, 87-184 (2008).
Rossi, E.A., et al, "In vivo imaging of retinal pigment epithelium cells in age related macular degeneration.," Biomed. Opt. Express, vol. 4, No. 11, pp. 2527-2539, Jan. 2013.
Rowe, M., et al, "Polarization-difference imaging: a biologically inspired technique for observation through scattering media," Optics Letters, vol. 20, No. 6, 3 pages (1995).
Schechner, Y., "Multiplexing for Optimal Lighting," IEEE Transactions on Pattern Analysis and Machine Intelligence, vol. 29, No. 8, 1339-1354 (2007).
Schnars, U., et al, "Digital recording and numerical reconstruction of holograms," Measurement Science and Technology, 13, R85 (2002).
Schwarz, C., et al, "Imaging interferometric microscopy," Optics letters 28, pp. 1424-1426 (2003).
Shechner, Y., et al, "Polarization-based vision through haze," Applied Optics 42(3), (2003).
Shechtman, Y., et al, "Sparsity based sub-wavelength imaging with partially incoherent light via quadratic compressed sensing," Opt Express 19:14807-14822 (2011).
Siegel, R., et al, "Cancer statistics 2013," CA: a cancer journal for clinicians, 2013. 63(1): p. 11-30.
Stoecker, W., et al, "Diagnostic Inaccuracy of Smartphone Applications for Melanoma Detection: Representative Lesion Sets and the Role for Adjunctive Technologies," JAMA Dermatology, 2013. 149(7): p. 884.
Sun, D., et al, "Estimating a signal from a magnitude spectrogram via convex optimization," arXiv:1209.2076 (2012).
Sun, J., et al, "Coded multi-angular illumination for Fourier ptychography based on Hadamard codes," 5 pages (2015).
Tam, K., et al, "Tomographical imaging with limited-angle input," J. Opt. Soc. Am. 21 (1981).
Thibault, P. et al, "Probe retrieval in ptychographic coherent diffractive imaging," Ultramicroscopy 109(4), 338-343 (2009).

(56) References Cited

OTHER PUBLICATIONS

Thibault, P., et al, "High-resolution scanning X-ray diffraction microscopy," Science 321, 2008, pp. 379-382.
Thomas, L., et al, "Semiological value of ABCDE criteria in the diagnosis of cutaneous pigmented tumors," Dermatology, 1998. 197(1): p. 11-17.
Tian, L., et al, "Multiplexed Coded Illumination for Fourier Ptychography with an LED Array Microscope," Optical Society of America, 14 pages (2014).
Tippie, A.E., et al, "High-resolution synthetic-aperture digital holography with digital phase and pupil correction," Opt. Express 19, pp. 12027-12038 (2011).
Turpin, T., et al, "Theory of the synthetic aperture microscope," pp. 230-240 (1995).
Tyson, R., "Principles of Adaptive Optics" (CRC Press, 2010).
Vulovic, M., et al, "When to use the projection assumption and the weak-phase object approximation in phase contrast cryo-EM," Ultramicroscopy 136 (2014) 61-66.
Waldspurger, I., et al, "Phase recovery, maxcut and complex semidefinite programming," Mathematical Programming 149, No. 1-2 (2015): 47-81.
Wang, Q., et al, "Adaptive Optics Microperimetry and OCT Images Show Preserved Function and Recovery of Cone Visibility in Macular Telangiectasia Type 2 Retinal Lesions," Invest. Ophthalmol. Vis. Sci., vol. 56, pp. 778-786, 2015.
Wang, Z., et al, "Tissue refractive index as marker of disease," Journal of Biomedical Optics 16, 116017-116017 (2011).
Watanabe, M., et al, "Telecentric optics for focus analysis," IEEE trans. pattern. anal. mach. intell., 19 1360-1365 (1997).
Wesner, J., et al, "Reconstructing the pupil function of microscope objectives from the intensity PSF," in Current Developments in Lens Design and Optical Engineering III, R. E. Fischer, W. J. Smith, and R. B. Johnson, eds., Proc. SPIE 4767, 32-43 (2002).
Williams, A., et al, "Fourier ptychographic microscopy for filtration-based circulating tumor cell enumeration and analysis," J. Biomed. Opt. 19(6), 066007 (2014).
Wolf, J., et al, "Diagnostic Inaccuracy of Smartphone Applications for Melanoma Detection," JAMA Dermatology, 2013, 149(7): p. 885-885.
Wu, J., et al, "Focal plane tuning in wide-field-of-view microscope with Talbot pattern illumination," Opt. Lett. 36, 2179-2181 (2011).
Wu, J., et al, "Wide field-of-view microscope based on holographic focus grid illumination," Opt. Lett. 35, 2188-2190 (2010).
Xu, W., et al, "Digital in-line holography for biological applications," Proc. Natl Acad. Sci. USA 98, pp. 11301-11305 (2001).
Yuan, C., et al, "Angular multiplexing in pulsed digital holography for aperture synthesis," Optics Letters 33, pp. 2356-2358 (2008).
Zeiss, C., "Microscopy, Cells Need The Perfect Climate, System Solutions for Live Cell Imaging under Physiological Conditions," printed Feb. 2008, 1-42 pgs.
Zhang, Y., et al, "Self-learning based fourier ptychographic microscopy," Optics Express, 16pgs (2015).
Zhang, Y., et al, "Photoreceptor Perturbation Around Subretinal Drusenoid Deposits as Revealed by Adaptive Optics Scanning Laser Ophthalmoscopy," Am. J. Ophthalmol., vol. 158, No. 3, pp. 584-596, 2014.
Zheng, G., et al, "Characterization of spatially varying aberrations for wide field-of-view microscopy," Opt. Express 21, 15131-15143 (2013).
Zheng, G., et al, "Microscopy refocusing and dark-field imaging by using a simple LED array," Opt. Lett. 36, 3987-3989 (2011).
Zheng, G., et al, "0.5 gigapixel microscopy using a flatbed scanner," Biomed. Opt. Express 5, 1-8 (2014).
Zheng, G., et al, "Sub-pixel resolving optofluidic microscope for on-chip cell imaging," Lab Chip 10, pp. 3125-3129 (2010).
Zheng, G. "The ePetri dish, an on-chip cell imaging platform based on subpixel perspective sweeping microscopy (SPSM)," Proc. Natl. Acad. Sci. USA 108, pp. 16889-16894 (2011).
Zheng, G., et al, "Wide-field, high-resolution Fourier ptychographic microscopy," Nature Photonics, vol. 7, pp. 739-745, Published Online Jul. 28, 2013 at www.nature.com/naturephotonics.
U.S. Appl. No. 15/160,941, filed May 20, 2016 entitled "Laser-Based Fourier Ptychographic Imaging Systems and Methods".
U.S. Notice of Allowance dated Aug. 23, 2016 in U.S. Appl. No. 14/466,481.
U.S. Office Action dated Aug. 16, 2016 in U.S. Appl. No. 14/065,280.
U.S. Office Action dated Sep. 16, 2016 I U.S. Appl. No. 14/065,305.
International Search Report and Written Opinion dated May 4, 2016 issued in PCT/US2016/015001.
International Search Report and Written Opinion dated May 11, 2016 issued in PCT/US2016/015002.
International Search Report and Written Opinion dated Jun. 27, 2016 issued in PCT/US2016/022116.
International Search Report and Written Opinion dated Jun. 30, 2016 issued in PCT/US2016/014343.
International Search Report and Wrtitten Opinion dated Sep. 5, 2016 issued in PCT/US2016/033638.
Chinese Office Action [Description in English] dated Jul. 11, 2016 issued in Application No. CN 201380068831.6.
Dierolf, M., et al, "Ptychographic X-ray computed tomography at the nanoscale," Nature, vol. 467, pp. 436-439, (2010).
Chung, J., et al, "Wide-field Fourier ptychographic microscopy using laser illumination source," Optical Society of America, 13 pgs., Mar. 23, 2016.
Guo, K., et al, "Optimization of sampling pattern and the design of Fourier ptychographic illuminator," Optical Society of America; Optics Express , vol. 23, No. 5, pp. 6171-6180 (2015).
Phillips, Z., et al, "Multi-Contrast Imaging and Digital Refocusing on a Mobile Microscope with a Domed LED Array," PLoS One, 10 (5), pp. 1-13 (2015).
Horstmeyer, R., et al, "Standardizing the resolution claims for coherent microscopy," Nature Photonics, vol. 10, pp. 68-71, Feb. 2016.
Horstmeyer, R., et al, "Solving ptychography with a convex relaxation," New Journal of Physics, vol. 17 (2015) 1-14 pages.
U.S. Notice of Allowance dated Nov. 2, 2016 in U.S. Appl. No. 14,572,493.
U.S. Office Action dated Nov. 22, 2016 in U.S. Appl. No. 15/003,559.
U.S. Supplemental Notice of Allowance dated Dec. 12, 2016 in U.S. Appl. No. 14/572,493.
U.S. Notice of Allowance dated Jan. 13, 2017 in U.S. Appl. No. 14/065,305.
U.S. Office Action dated Feb. 21, 2017 in U.S. Appl. No. 14/960,252.
U.S. Supplemental Notice of Allowability dated Mar. 2, 2017 in U.S. Appl. No. 14/065,305.
U.S. Notice of Allowance dated Mar. 8, 2017 in U.S. Appl. No. 14/572,493.
U.S. Office Action dated Mar. 13, 2017 in U.S. Appl. No. 14/658,019.
Chinese Office Action [Description in English] dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Applicatoin No. 14832857.8.
Lu, H., et al, "Quantitative phase imaging and complex field reconstruction by pupil modulation differential phase contrast," Optics Express, vol. 24, No. 22, pp. 25345-25361 (Oct. 31, 2016).
Ou, X., et al, "Aperture scanning Fourier ptychographic microscopy," Biomedical Optics Express, vol. 7, No. 8, pp. 3140-3150 (Aug. 1, 2016).
Horstmeyer, R., et al, "Diffraction tomography with Fourier ptychography," Optica, vol. 3, No. 8, pp. 827-835 (Aug. 2016).
Bian, L., et al, "Fourier ptychographic reconstruction using Poisson maximum likelihood and truncated Wirtinger gradient," NPG: Scientific Reports 6, article No. 27384, Jun. 10, 2016, pp. 1-10.
Wu, J., et al, "Harmonically matched grating-based full-field quantitative high-resolution phase microscope for observing dynamics of

(56) References Cited

OTHER PUBLICATIONS transparent biological samples," Optical Society of America, vol. 15, No. 26, pp. 18141-18155 (Dec. 19, 2007).
Wu, J., et al, "Paired-angle-rotation scanning optical coherence tomography forward-imaging probe," Optics Letters, vol. 31, No. 9, pp. 1265-1267 (May 2006).
Kawata, S. et al, "Optical microscope tomography. I. Support constraint," Journal Optical Society America A, vol. 4, No. 1, pp. 292-297, Jan. 1, 1987.
U.S. Office Action dated Mar. 24, 2017 in U.S. Appl. No. 14/710,947.
U.S. Notice of Allowance dated Mar. 31, 2017 in U.S. Appl. No. 14/572,493
U.S. Final Office Action dated Apr. 3, 2017 in U.S. Appl. No. 14/065,280
Chinese Second Office Action [Description in English] dated Feb. 17, 2017 issued in Application No. CN201380068831.6
Kim, M., et al, "High-speed synthetic aperture microscopy for live cell imaging," Optics Letters, vol. 36, No. 2, Jan. 15, 2011, pp. 148-150. <doi:10.1364/OL.36.000148>.
Chai, A., et al, "Array imaging using intensity-only measurements," IOP Publishing: Inverse Problems, vol. 27, No. 1, Jan. 2011, pp. 1-16. <doi:10.1088/0266-5611/27/1/015005> [Retrieved on Mar. 24, 2017] [URL: http://www.stacks.iop.org/IP/27/015005].
Zheng, G., "Fourier Ptychographic Imaging: A MATLAB tutorial," IOP Concise Physics, Morgan & Claypool, May 2016, pp. 96. <ISBN: 978-1-6817-4272-4> <doi: 10.1088/978-1-6817-4273-1>.
U.S. Office Action dated May 19, 2017 in U.S. Appl. No. 15/081,659.
International Preliminary Report on Patentability dated Jun. 15, 2017 issued in Application No. PCT/US2015/064126.
U.S. Notice of Allowance dated Jun. 9, 2017 in U.S. Appl. No. 14/065,305.
U.S. Notice of Allowance dated Jun. 9, 2017 in U.S. Appl. No. 15/206,859.
U.S. Notice of Allowance dated Jun. 20, 2017 in U.S. Appl. No. 14/572,493.
Preliminary Amendment dated Apr. 22, 2016 filed in U.S. Appl. No. 15/081,659.
Preliminary Amendment dated Jun. 24, 2016 filed in U.S. Appl. No. 15/081,659.
Preliminary Amendment dated Mar. 17, 2014 filed in U.S. Appl. No. 14/065,280.
Preliminary Amendment dated Apr. 25, 2016 filed in U.S. Appl. No. 14/710,947.
Preliminary Amendment dated Nov. 28, 2016 filed in U.S. Appl. No. 15/206,859.
Preliminary Amendment dated Mar. 17, 2014 filed in U.S. Appl. No. 14/065,305.
Preliminary Amendment dated Nov. 28, 2016 filed in U.S. Appl. No. 15/209,604.
U.S. Supplemental Notice of Allowance dated Jun. 28, 2017 in U.S. Appl. No. 15/206,859.
U.S. Final Office Action dated Jul. 27, 2017 in U.S. Appl. No. 15/003,559.
U.S. Notice of Allowance dated Aug. 16, 2017 in U.S. Appl. No. 15/209,604.
U.S. Notice of Allowance dated Sep. 1, 2017 in U.S. Appl. No. 15/206,859.
European Office Action dated May 16, 2017 issued in European Patent Application No. 13851670.3.
International Preliminary Report on Patentability dated Jul. 6, 2017 issued in Application No. PCT/US2015/067498.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
International Preliminary Report on Patentability dated Aug. 10, 2017 issued in Application No. PCT/US2016/015002.
Hoppe, W., "Diffraction in inhomogeneous primary wave fields. 1. Principle of phase determination from electron diffraction interference." Acta Crystallographica Section a-Crystal Physics Diffraction Theoretical and General Crystallography, A25, Jan. 1, 1969, pp. 495-501. (English Machine Translation Incl.).
Reinhard, E., et al, "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.
Tian, L., et al, "3D differential phase-contrast microscopy with computational illumination using an LED array," Optics Letters, vol. 39, No. 5, Mar. 1, 2014, pp. 1326-1329. <doi:10.1364/OL39. 001326>.
Tian, L., et al, "Computional illumination for high-speed in vitro Fourier ptychographic microscropy," Optica: Research Article, vol. 2, No. 10, Oct. 14, 2015, pp. 904-911. <doi:10.1364/OPTICA.2. 000904>.
Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Office Action dated Aug. 31, 2017 in U.S. Appl. No. 15/636,494.
Unpublished U.S. Appl. No. 15/620,674, filed Jun. 12, 2017, Chung et al.
Unpublished U.S. Appl. No. 15/636,494, filed Jun. 28, 2017, Kim et al.
Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.

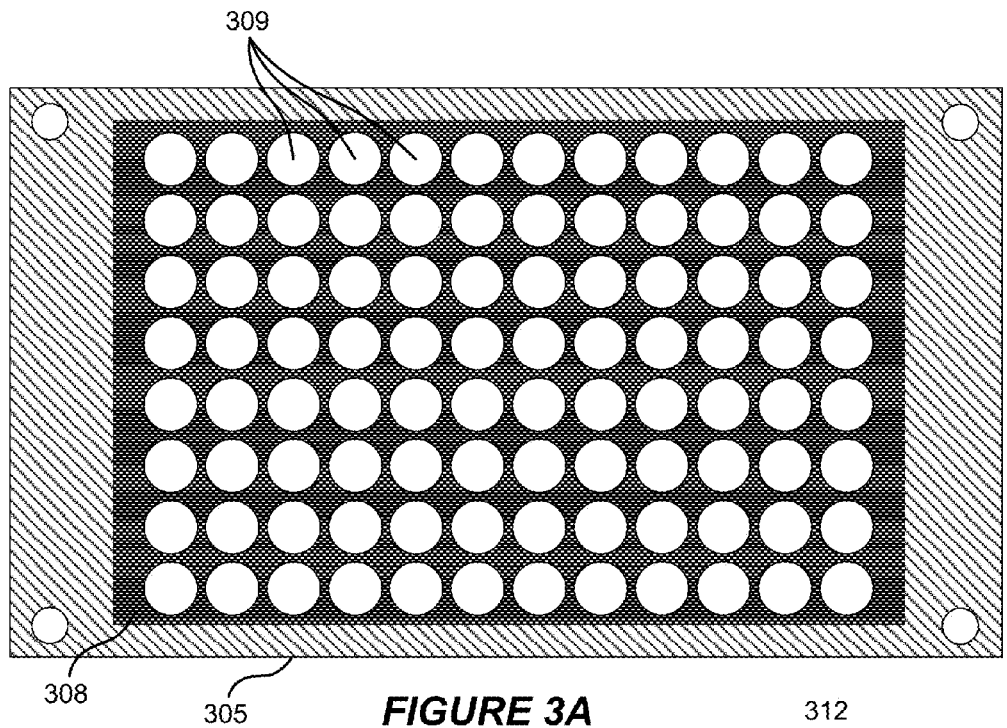
FIGURE 3A
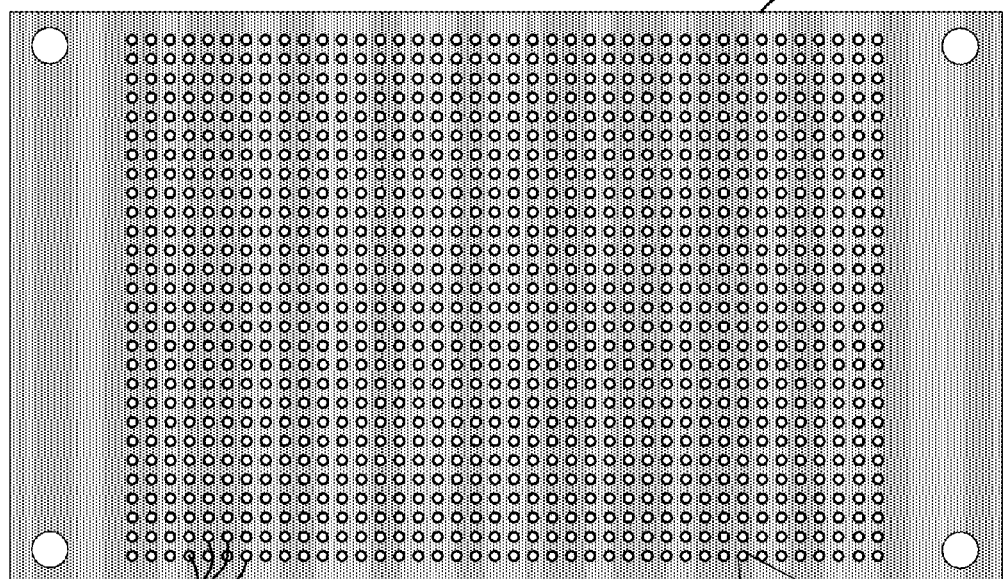
FIGURE 3B
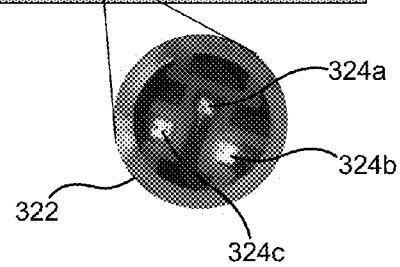

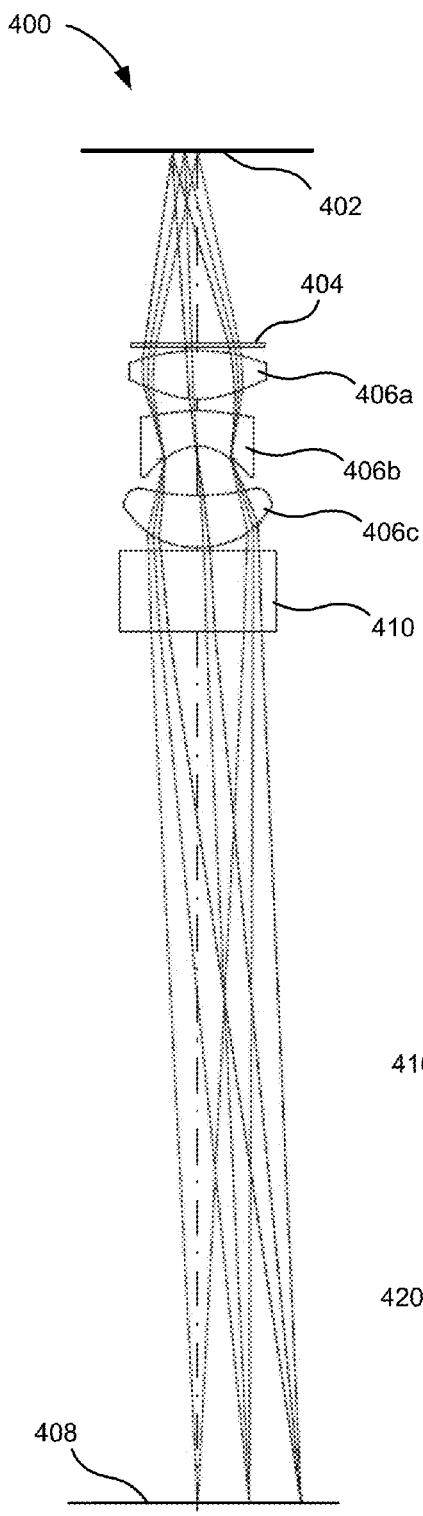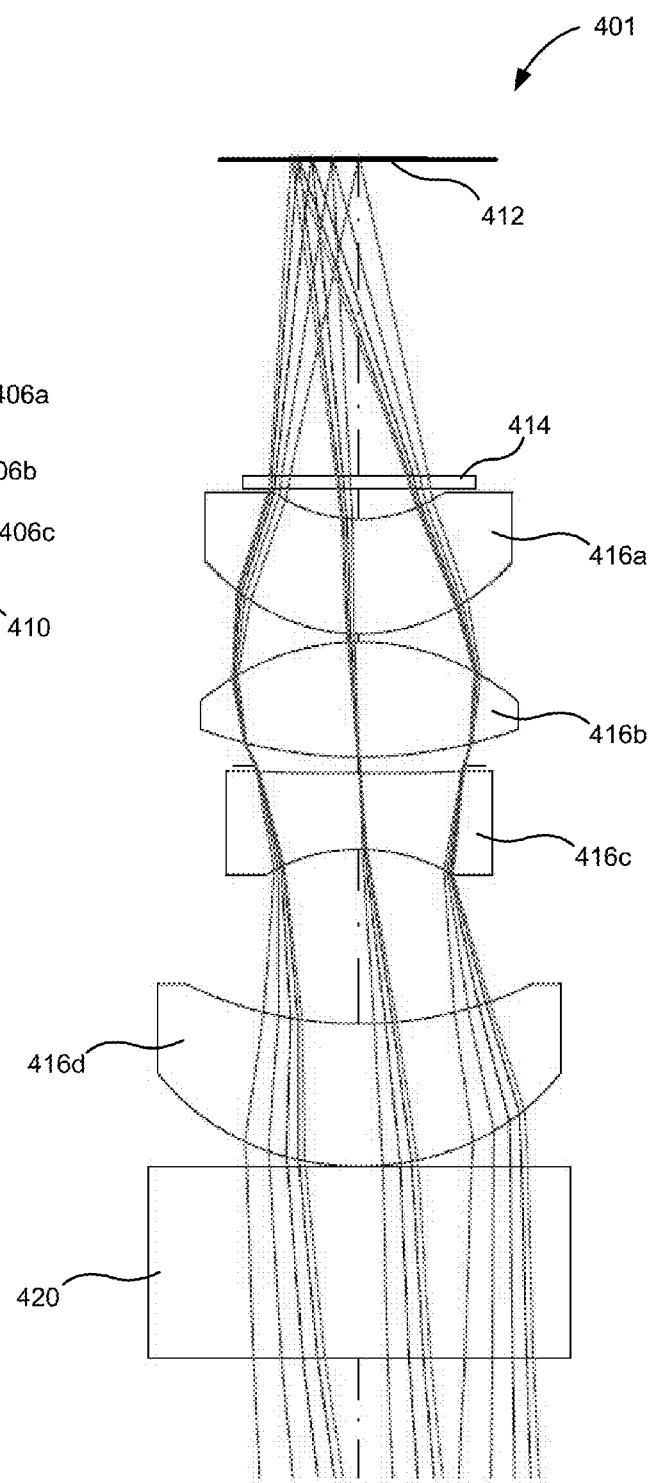
*FIGURE 4A*  *FIGURE 4B*

ARRAY LEVEL FOURIER PTYCHOGRAPHIC IMAGING

PRIORITY DATA

This non-provisional application claims the benefit of priority under 35 U.S.C. 119(e) to U.S. provisional patent application No. 62/107,628 titled "Development of 96-well Plate Fluorescence Imaging System" by Kim et. al. and filed on 26 Jan. 2015, and to U.S. provisional patent application No. 62/107,631 titled "Real-time Cell Culture Monitoring via Fourier Ptychographic Microscopy" by Kim et. al. and filed on 26 Jan. 2015, both of which are hereby incorporated by reference herein in their entireties and for all purposes. This application also is related to U.S. patent application Ser. No. 15/007,159 by Kim et al. and filed on the same day as the present application, which is hereby incorporated by reference in its entirety and for all purposes.

FEDERALLY SPONSORED RESEARCH OR DEVELOPMENT

This invention was made with government support under Grant No. OD007307 awarded by the National Institutes of Health. The government has certain rights in the invention.

TECHNICAL FIELD

This disclosure relates generally to digital imaging, and more specifically to Fourier ptychographic (FP)-based techniques for imaging an array of sample wells in parallel.

BACKGROUND

Multi-well plate readers are key pieces of bioscience equipment used to quickly obtain fluorescence and absorbance information from samples such as live cultures grown in multi-well plates (for example, 96 well plates). A typical reader takes 10 seconds to acquire a complete set of fluorescence or absorbance measurements. However, conventional plate readers do not provide any image information. This represents a significant loss or discarding of image information. For example, imaging of samples including live tissue cultures can reveal cell structure and health information that can provide a wealth of insight to the user. For example, image information of a well that returns a negative fluorescence signal in a toxicity screen can quickly inform a user as to whether the negative signal is due to the cell death, compromised growth, contamination, or other reasons. Generally, to collect image information, the multi-well plate would have to be put into a second sophisticated system that uses a microscope to slowly scan and image each well of the plate individually on a sequential basis. Because such conventional techniques are based on a singular microscope, the process is very slow. The complete process can take upwards of approximately 150 minutes or more for an entire multi-well plate. Such a significant amount of machine time is an inefficient and prohibitive if numerous multi-well plates are to be imaged, for example, because such latency can compromise the time schedule of the experiment design. In view of these constraints, it is not surprising that users often only take this extra imaging measurement step for a small fraction of the samples, or when situations absolutely demand imaging.

SUMMARY

Certain aspects of this disclosure pertain to Fourier ptychographic imaging systems and methods.

In one aspect an imaging system includes: an illumination system including an array of light sources; an optical system including one or more lens arrays, each of the lens arrays including an array of lenses, each of the lenses in each of the one or more lens arrays in alignment with a corresponding set of light sources of the array of light sources; an imaging system including an array of image sensors, each of the image sensors in alignment with a corresponding lens or set of lenses of the one or more lens arrays, each of the image sensors configured to acquire image data based on the light received from the corresponding lens or set of lenses; a plate receiver system capable of receiving a multi-well plate including an array of wells, the plate receiver system configured to align each of the wells with a corresponding one of the image sensors; and a controller configured to control the illumination of the light sources and the acquisition of image data by the image sensors, the controller further configured to perform: an image acquisition process including a plurality of scans, each scan associated with a unique pattern of illumination, each of the image sensors configured to generate an image for a respective one of the wells during each scan; and an image reconstruction process during which the controller performs a fourier ptychographic operation to generate a reconstructed image for each of the wells based on the image data captured for the respective well during each of the scans.

In another aspect an imaging method performed by an imaging system is described, the imaging system including an illumination system including an array of light sources; an optical system including one or more lens arrays, each of the lens arrays including an array of lenses, each of the lenses in each of the one or more lens arrays in alignment with a corresponding set of light sources of the array of light sources; an imaging system including an array of image sensors, each of the image sensors in alignment with a corresponding lens or set of lenses of the one or more lens arrays, each of the image sensors configured to acquire image data based on the light received from the corresponding lens or set of lenses; a plate receiver system capable of receiving a multi-well plate including an array of wells, the plate receiver system configured to align each of the wells with a corresponding one of the image sensors; and a controller configured to control the illumination of the light sources and the acquisition of image data by the image sensors, the method comprising: performing an image acquisition process including a plurality of scans, each scan associated with a unique pattern of illumination, each of the image sensors configured to generate an image for a respective one of the wells during each scan; and performing an image reconstruction process during which the controller performs a fourier ptychographic operation to generate a reconstructed image for each of the wells based on the image data captured for the respective well during each of the scans.

These and other features are described in more detail below with reference to the associated drawings.

BRIEF DESCRIPTION OF THE DRAWINGS

FIG. 3A shows a top view of an example sample platform having a multi-well plate positioned thereon according to some implementations.

FIG. 3B shows a bottom view of an example illumination system according to some implementations.

FIG. 4A shows a diagram of a portion of an example optical arrangement including three lenses according to some implementations.

FIG. 4B shows a diagram of a portion of an example optical arrangement including four lenses according to some implementations.

DETAILED DESCRIPTION

Figure 1:
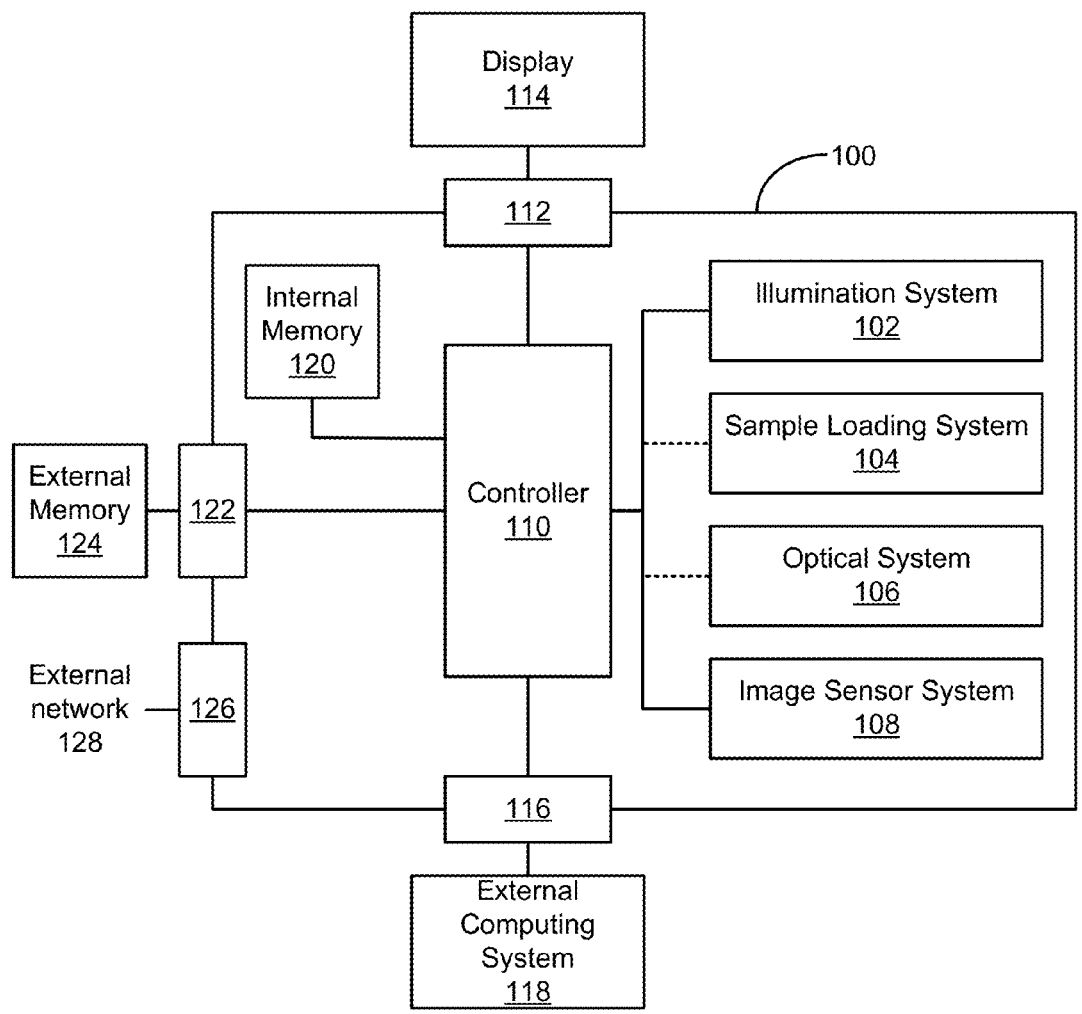
FIG. 1 shows a block diagram of an example imaging system capable of Fourier ptychographic (FP) imaging according to some implementations.

The following description is directed to certain implementations for the purposes of describing various aspects of this disclosure. However, a person having ordinary skill in the art will readily recognize that the teachings herein can be applied in a multitude of different ways. Thus, the teachings are not intended to be limited to the implementations depicted solely in the Figures, but instead have wide applicability as will be readily apparent to one having ordinary skill in the art.

As used herein, the conjunction "or" is intended herein in the inclusive sense where appropriate unless otherwise indicated; that is, the phrase "A, B or C" is intended to include the possibilities of A, B, C, A and B, B and C, A and C and A, B and C. Additionally, a phrase referring to "at least one of" a list of items refers to any combination of those items, including single members. As an example, "at least one of: A, B, or C" is intended to cover: A, B, C, A-B, A-C, B-C, and A-B-C.

I. Introduction

Various aspects relate generally to imaging systems, devices, and methods capable of use in Fourier ptychographic (FP) imaging, and more specifically, to imaging systems, devices, and methods configured to enable FP imaging at an array level. For example, particular implementations are directed to an imaging system configured to enable high resolution FP imaging of each well of a multi-well plate in parallel. Some implementations further relate to such an imaging system further configured to perform fluorescence imaging of each well of the multi-well plate in parallel.

Traditionally, the resolution of an image sensor, such as a camera system, determines the fidelity of visual features in the resultant images captured by the image sensor. However, the resolution of any image sensor is fundamentally limited by geometric aberrations in the lens or lenses used to focus light onto the image sensor. This is because the number of resolvable points for a lens, referred to as the SBP, is fundamentally limited by geometrical aberrations. While CMOS and CCD technologies have been demonstrated having imaging sensors with pixels in the 1 micron (μm) range, it remains a challenge to design and manufacture lenses which have the resolving power to match the resolution of such image sensors. This problem is further exacerbated in imaging systems that are to be configured to scan multiple samples in parallel, for example, because the lenses are very limited in diameter.

FP refers generally to an imaging technique that enables non-interferometric phase imaging and near-wavelength diffraction-limited resolution. FP generally requires the collection of multiple scans of an object (for example, a sample in a well), each scan being acquired using light at a different illumination angle than the other scans. The light can be generated from coherent light sources such as, for example, a light emitted diode (LED) array. The image data captured in the scans is then processed using a phase retrieval algorithm enabling an iterative reconstruction of the object into a higher resolution image. FP imaging is generally related to (conventional) ptychography in that it solves the phase problem by permuting the role of the real and the Fourier space by swapping the focusing element and the object. Among the advantages of FP imaging techniques are the capabilities to use imaging optics with lower numerical aperture, which increases the depth of focus, the working distance and the size of the field of view. FP imaging techniques also enable the correction of lens aberrations, leading to a much larger space-bandwidth product (SBP) (the mathematical product of the resolution and the exploitable size of an image).

Some examples of microscope systems and methods using FP imaging techniques are discussed in "Wide-field, high-resolution Fourier ptychographic microscopy," Nat. Photonics 7(9), 739-745 (2013), X. Ou, R. Horstmeyer, C. Yang, and G. Zheng, "Quantitative phase imaging via Fourier ptychographic microscopy," Opt. Lett. 38(22), 4845-

4848 (2013), R. Horstmeyer and C. Yang, "A phase space model of Fourier ptychographic microscopy," Opt. Express 22(1), 338-358 (2014), X. Ou, G. Zheng, and C. Yang, "Embedded pupil function recovery for Fourier ptychographic microscopy," Opt. Express 22(5), 4960-4972 (2014), X. Ou, R. Horstmeyer, G. Zheng, and C. Yang, "High numerical aperture Fourier ptychography: principle, implementation and characterization," Opt. Express 23(3), 3472-3491 (2015), J. Chung, X. Ou, R. P. Kulkarni, and C. Yang, "Counting White Blood Cells from a Blood Smear Using Fourier Ptychographic Microscopy," PLoS One 10(7), e0133489 (2015), A. Williams, J. Chung, X. Ou, G. Zheng, S. Rawal, Z. Ao, R. Datar, C. Yang, and R. Cote, "Fourier ptychographic microscopy for filtration-based circulating tumor cell enumeration and analysis," J. Biomed. Opt. 19(6), 066007 (2014), and R. Horstmeyer, X. Ou, G. Zheng, P. Willems, and C. Yang, "Digital pathology with Fourier ptychography," Comput. Med. Imaging Graphics 42, 38-43 (2015), which are hereby incorporated by reference for the discussion.

As introduced above, various aspects of this disclosure relate to imaging systems, devices and methods for implementing FP processing techniques to obtain high-resolution images of an entire array of samples in parallel at the array level. To implement the FP techniques, each of the imaging systems described herein generally includes an illumination system, a sample loading system, an optical system and an imaging system. The illumination system generally includes an array of light sources, the optical system generally includes one or more arrays of lenses, and the imaging system generally includes an array of image sensing devices. In some example implementations, the sample loading system is configured to receive a multi-well plate including a plurality of sample wells, each of which contains a sample of interest. The imaging system can further include a controller for selectively turning on (or "powering," "actuating" or "illuminating") particular ones, subsets or patterns of the light sources to provide plane wave illumination of each of a plurality of the wells simultaneously during a scanning operation ("scan"). A plurality of scans are performed over the course of an entire image acquisition phase using different patterns of illumination such that each of the wells is illuminated at a plurality of incidence angles by the time the image acquisition phase is complete.

The lenses of the optical system focus light scattered or emitted by the samples in response to the illumination onto corresponding image sensors. Each image sensor is configured to capture a relatively low-resolution image of a region of a corresponding one of the wells based on the light it receives from the respective lens or lenses of the optical system. Over the course of the entire image acquisition phase, each image sensor generates a sequence of intensity distribution measurements (raw intensity images), one image being generated for each of the scans. A processing device combines the relatively low-resolution raw intensity images for each of the wells in the spatial frequency domain using a Fourier ptychographic reconstruction process to correct aberrations and to render a single high-resolution image for each of the wells. In particular aspects, the processing device performs the Fourier ptychographic reconstruction processing on each of the wells individually but in parallel with the processing of the image data captured from the other ones of the wells enabling the parallel generation of a high-resolution image for each of the wells concurrently (or "simultaneously"). The FP approach also enables digitally refocusing of the resultant reconstructed images, for example, even if the system misses the focal plane by as much as 0.3 mm or more. Digital refocusing is particularly useful as it simplifies the process of imaging—the well plate does not need to be as precisely placed in order to get high resolution images.

II. Imaging System for Fourier Ptychographic (FP) Imaging and Fluorescent Imaging FIG. 1 shows a block diagram of an example imaging system 100 capable of Fourier ptychographic (FP) imaging according to some implementations. At a high level, the imaging system 100 is configured or configurable to scan an array of samples at the array level; that is, to illuminate and capture images of an entire array of samples in parallel. The imaging system 100 also can include parallel processing capabilities to transform and combine raw image data frames obtained for each of the sample wells to generate an FP-reconstructed image for each of the sample wells at the array level. The imaging system 100 includes an illumination system 102, a sample loading system 104, an optical system 106 and an image sensor system 108. A controller 110 controls the operations of the illumination system 102 and the image sensor system 108. The controller 110 also is configured to receive the raw (or minimally pre-processed) image data from the image sensor system 108. In some implementations, the controller 110 is further configured to execute one or more algorithms on the raw image data to perform one or more processing operations such as various FP imaging processes including aberration correction.

The illumination system 102 includes an array (or "matrix") of light sources. For example, each light source can include one or more light-emitting diodes (LEDs). The controller 110 controls the illumination of the light sources, for example, by selectively powering on or otherwise allowing only particular ones or subsets of the light sources to form various illumination patterns at particular times and for particular durations during various imaging scans. The optical system 106 generally includes at least one array of lenses (referred to hereinafter as a "lens array"). Each lens array includes a plurality (or "multiplicity") of lenses. The image sensor system 108 includes an array of image sensors, for example, an array of cameras or other suitable imaging devices. In various implementations, the arrangement and total number T of lenses in each array matches the arrangement and total number of image sensors in the imaging system as well as the arrangement and total number of wells in a multi-well plate to be imaged.

The sample loading system 104 is generally configured to receive a sample array such as a conventional or commercially-available multi-well plate (also referred to as a "well plate," "microtiter plate," "microplate," or "microwell plate"). Each multi-well plate generally includes an array (typically a rectangular array) of wells arranged in a plurality of rows and a plurality of columns. In typical applications, samples are generally pipetted or otherwise deposited into the wells for imaging. In various implementations, the sample loading system 104 is more specifically configured to receive a multi-well plate inserted or otherwise loaded into the sample loading system 104 such that the wells (for example, the bottom surfaces of the wells) of the multi-well plate are positioned along a particular plane between the light sources of the illumination system 102 and the lenses of the optical system 106. The sample loading system 104 also functions to approximately align the centers of the wells of the multi-well plate with the centers of corresponding lenses of the optical system 106 (although as will become clear below, precise alignment is not required for various implementations of the imaging system described herein).

During a scanning operation, light generated by the illumination system 102 illuminates samples in the wells. In some imaging modes or processes, such as those for use in FP imaging or other bright-field imaging, the light incident on each sample is scattered by the physical features of the sample as it passes through the sample. In some other imaging modes or processes, such as those for use in fluorescence imaging, the light sources are configured to generate particular wavelengths of excitation light to excite fluorophores (for example, specialized proteins) in the sample. In such fluorescence imaging, the incident excitation light imparts energy into the fluorophores, which then emit light at lower energy wavelengths. A portion of the scattered light or emitted light then passes through the transparent bottom of the well to a corresponding lens (or set of lenses) of the optical system 106. The lens(es) below each respective well generally function to focus the scattered or emitted light from the well onto a respective one of the image sensors of the image sensor system 108. Each image sensor is configured to capture the light and output a data signal including image data representative of the intensities of light received at particular locations of the image sensor (referred to herein as a "light intensity distribution," "intensity distribution," or simply as an "image" or "image frame").

The image data output by each of the image sensors is then transmitted (or "sent" or "communicated") to the controller 110. In some implementations, the controller 110 is configured to process the raw image data of each scan to generate processed image data. For example, in some implementations the controller 110 is configured or configurable by a user to perform one or more FP image processing operations on the raw image data. As described above, to generate an FP-reconstructed image of each well in parallel, a plurality of scans are performed using different illumination patterns. The controller 110 interprets image data from the sequence of acquired intensity images, transforms the relatively low resolution image data frames associated with each of the scans into fourier space, combines the transformed raw image data, corrects for aberrations resulting from the lenses as well as the sample features, and generates a single high resolution image for each of the sample wells. As described above, the imaging system 100 also can be configured to perform fluorescence imaging. As such, the controller 110 can generally include functionality to interpret, process, and in some instances combine fluorescence image data for each of the sample wells in parallel.

To perform such parallel image processing, the controller 110 generally includes at least one processor (or "processing unit"). Example processors include, for example, one or more of a general purpose processor (CPU), an application-specific integrated circuit (ASIC), an programmable logic device (PLD) such as a field-programmable gate array (FPGA), or a System-on-Chip (SoC) that includes one or more of a CPU, ASIC, PLD as well as a memory and various interfaces. The controller 110 also is in communication with at least one internal memory device 120. The internal memory device 120 can include a non-volatile memory array for storing processor-executable code (or "instructions") that is retrieved by the processor to perform various functions or operations described herein for carrying out various algorithms or other operations on the image data. The internal memory device 120 also can store raw and/or processed image data (including FP-reconstructed images). In some implementations, the internal memory device 120 or a separate memory device can additionally or alternatively include a volatile memory array for temporarily storing code to be executed as well as image data to be processed, stored, or displayed. In some implementations, the controller 110 itself can include volatile and in some instances also non-volatile memory.

In some implementations, the controller 110 is configured or configurable by a user to output raw image data or processed image data (for example, after FP image processing) over a communication interface 112 for display on a display 114. In some implementations, the controller 110 also can be configured or configurable by a user to output raw image data as well as processed image data (for example, after FP image processing) over a communication interface 116 to an external computing device or system 118. Indeed in some implementations, one or more of the FP imaging operations can be performed by such an external computing device 118. In some implementations, the controller 110 also can be configured or configurable by a user to output raw image data as well as processed image data (for example, after FP image processing) over a communication interface 122 for storage in an external memory device or system 124. In some implementations, the controller 110 also can be configured or configurable by a user to output raw image data as well as processed image data (for example, after FP image processing) over a network communication interface 126 for communication over an external network 128 (for example, a wired or wireless network). The network communication interface 126 also can be used to receive information such as software or firmware updates or other data for download by the controller 110. In some implementations, the imaging system 100 further includes one or more other interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that one or more of the illumination system 102 and the image sensor system 108 can be electrically coupled to communicate with the controller over one or more of a variety of suitable interfaces and cables such as, for example, USB interfaces and cables, ribbon cables, Ethernet cables, among other suitable interfaces and cables.

The data signals output by the image sensors may in some implementations be mutliplexed, serialized or otherwise combined by a multiplexer, serializer or other electrical component of the image sensor system before being communicated to the controller 110. In such implementations, the controller 110 can further include a demultiplexer, deserializer or other device or component for separating the image data from each of the image sensors so that the image frames for each of the sample wells can be processed in parallel by the controller 110.

Figure 2A:
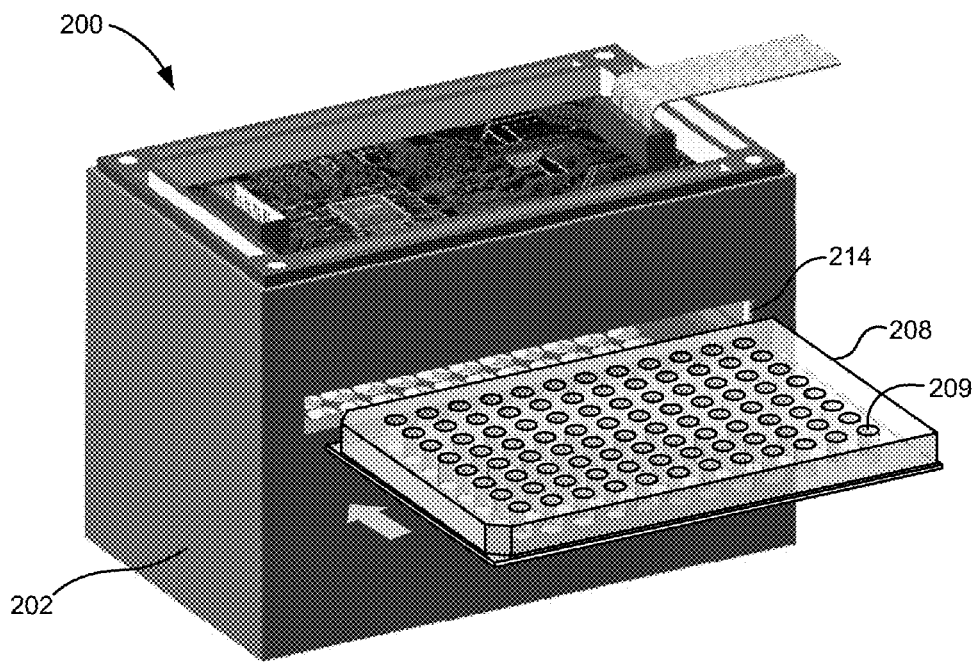
FIG. 2A shows a schematic diagram of an example imaging system capable of FP imaging according to some implementations.
Figure 2B:
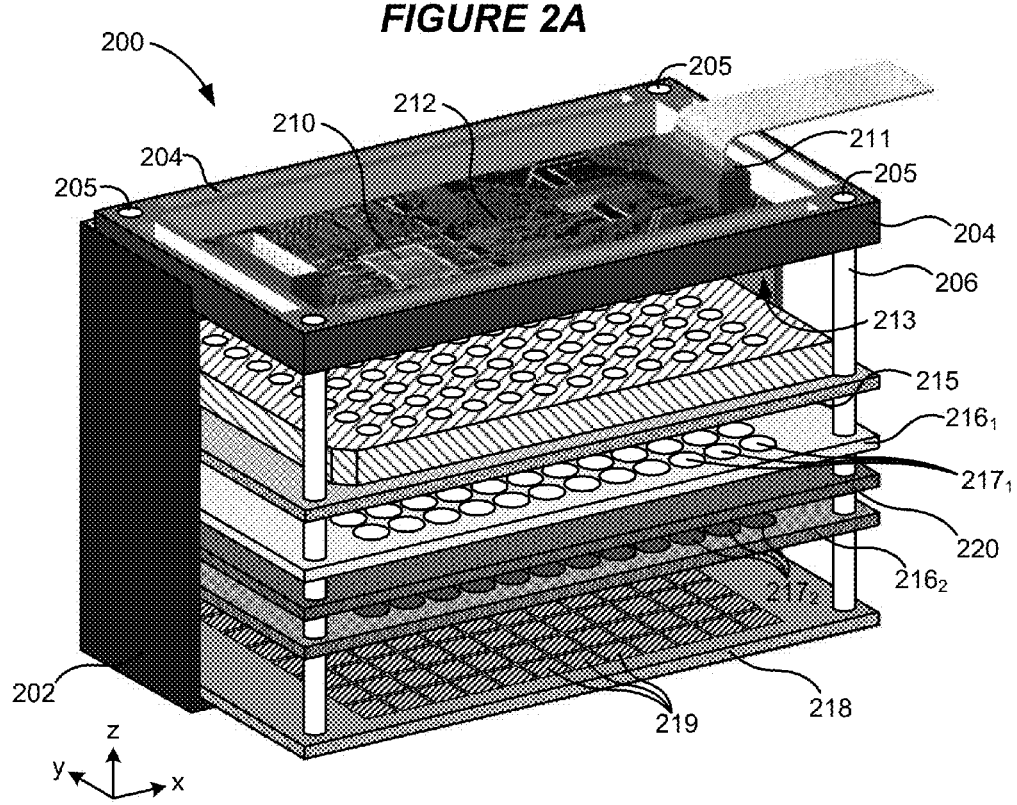
FIG. 2B shows a cross-sectional perspective view of the imaging system of FIG. 2A.

FIG. 2A shows a schematic diagram of an example imaging system 200 capable of FP imaging according to some implementations. FIG. 2B shows a cross-sectional perspective view of the imaging system 200 of FIG. 2A. The imaging system 200 of FIG. 2 is an example of a physical implementation of the imaging system 100 of FIG. 1. The imaging system 200 generally includes a housing or enclosure 202. In some implementations, the enclosure 202 is formed of a metal, metallic alloy or plastic material. In some implementations, the enclosure 202 is formed of an optically opaque material and/or painted or otherwise coated in an optically opaque layer to prevent (or "block" or "shield") ambient or other externally-generated light from illuminating the samples or the image sensors. This light shielding can be especially important in fluorescence imaging where the intensity of the emitted light is relatively much lower than that of the excitation light and decays rapidly.

In some implementations, the enclosure 202 surrounds a frame structure 204. In the illustrated implementation, the frame structure 204 provides a rigid frame from which the various components of the imaging system 200 can be supported. In some implementations, the frame structure 204 is formed of a metal, metallic alloy or plastic material. In some implementations, the frame structure 204 also is formed of an optically opaque material and/or painted or otherwise coated in an optically opaque layer. In some implementations, the enclosure 202 and the frame structure 204 are integrally formed together. In some other implementations, the enclosure 202 and the frame structure 204 are assembled together by screws, bolts, rivets, glue or other devices or materials so as to be rigidly fixed together. In the illustrated implementation, the frame structure 204 includes alignment through-holes 205 through which frame alignment rods 206 are passed and positioned. In some implementations, the frame alignment rods 206 also are formed of a metal, metallic alloy or plastic material.

In some implementations, each of the illumination system, the sample loading system, the optical system and the image sensor system are physically supported by one or more of the enclosure 202, the frame structure 204 and the frame alignment rods 206 so as to be rigidly fixed in relative position and at particular distances from one another. In some implementations, each of the illumination system, the sample loading system, the optical system and the image sensor system includes one or more substrates having corresponding through-holes. For example, the illumination system can include a circuit board or other dielectric substrate 212. The array of light sources 213 (hidden from view in FIG. 2A or 2B but indicated by an arrow as being under the circuit board 212) can be electrically and physically coupled onto or into the circuit board 212. Conductive leads of the light sources 213 can be electrically coupled with the controller 210 via conductive traces printed or otherwise deposited on a first or upper surface of the circuit board 212 while the light-emitting portions of the light sources 213 can be oriented so as to radiate light away from a second or lower surface of the circuit board 212 toward the lenses of the optical system. In the illustrated implementation, a controller 210 (for example, implementing controller 110 of FIG. 1) is mounted on the same circuit board 212 as the light sources 213. In some other implementations, the controller 210 can be mounted onto a separate circuit board that is electrically coupled with the circuit board 212 and thereby to the illumination system.

As described above, the optical system can include one or more lens arrays, for example, 1, 2, 3, 4 or more lens arrays depending on the particular application. In the illustrated implementation, the optical system includes two lens arrays $216_1$ or $216_2$ each of which includes a respective substrate into which are formed, assembled or positioned an array of lenses $217_1$ or $217_2$, respectively. The image sensor system can include a circuit board or other dielectric substrate 218. An array of image sensors 219 can be electrically and physically coupled onto or into the circuit board 218. The active light-sensitive regions of the image sensors 219 can be oriented away from a first or upper surface of the circuit board 218 toward the lenses of the optical system while the conductive leads of the image sensors 219 can be electrically coupled with the controller 210 via conductive traces printed or otherwise deposited on a second or lower surface of the circuit board 218 to a communication interface (for example, a USB interface) that is then connected with the controller 210 via a cable.

In such an arrangement, each of the frame alignment rods 206 can pass through corresponding through-holes in each of the substrates 212, 216 and 218 during assembly to align the light sources and respective ones of the lenses and images sensors along a vertical direction (for example, a z direction along a height of the imaging system 200). More specifically, the frame alignment rods 206 can ensure that each image sensor 219 is aligned with a corresponding lens in each of one or more stacked lens arrays, and that each of the lenses in each lens array are aligned with one another and with a set of one or more light sources 213. The enclosure 202 and/or frame structure 204 also can include guides, ribs, shelves or other supported mechanisms extending along inner surfaces of the enclosure or frame structure, respectively, to physically support the respective substrates 212, 216 and 218 at the proper distances from one another along the vertical z direction. Such an arrangement ensures that the light sources 213, lenses 217 and image sensors 219 are suitably positioned relative to one another to properly focus light scattered or emitted by the samples in the wells 209 onto the image sensors and, as described below, such that the angles of incidence of the light generated by the light sources can be precisely determined or otherwise known.

As described above, the sample loading system is generally configured to receive a sample array such as a conventional or commercially-available multi-well plate 208 including a rectangular array of wells 209 arranged in a plurality of rows and a plurality of columns. In the illustrated implementation, a sample array 208 can be loaded through an aperture slot 214 in the housing enclosure 202 and onto a sample platform 215 in the sample loading system. The sample platform 215 also can include through-holes into which the frame alignment rods 206 can pass to ensure that the sample platform 215 is aligned with the image sensor system, the optical system and the illumination system. Additionally, the sample platform 215 can include raised guides or ridges or other alignment mechanisms to ensure that a loaded multi-well plate 208 is properly oriented such the centers of each of the wells 209 are approximately aligned with the centers of the corresponding lenses 217 in the lens arrays 216 and with the centers of the image sensors 219. In some implementations, the sample loading system further includes a door that is coupled with the enclosure 202 or with the frame structure 204 via a sliding mechanism or a hinge mechanism enabling the door to be opened and closed with ease to insert and remove multi-well plates 208. In some implementations, the sample loading system can include a mechanical, electrical or electromechanical loading and ejecting mechanism that automatically pulls the multi-well plate 208 into the imaging system for imaging and that automatically ejects the multi-well plate when after the imaging has been performed. Such an automatic mechanism can be triggered electronically by a user via an input device (such as a keyboard or mouse), triggered by a button or touchscreen interface on the enclosure, or automatically by the controller 210 when it detects that a plate is being loaded or when it determines that an imaging operation is complete.

FIG. 3A shows a top view of an example sample platform 305 having a multi-well plate 308 positioned thereon according to some implementations. The multi-well plate 308 includes a number T of sample wells arranged in a plurality of R rows and C columns. Examples of commercially-available multi-well plates include the Costar® well plates manufactured by Corning®, the CELLSTAR® 96 W Microplate manufactured by Greiner, and the CytoOne® well plates. In the illustrated example, the multi-well plate includes 96 wells arranged in eight rows and twelve columns. In such an example, each of the wells can have a diameter of approximately 6 millimeters (mm). In some other implementations, the imaging system 200 can be configured to image other multi-well plate formats such as, for example, plates consisting of 6 wells, 12 wells, 96 wells, 384 wells, 1536 wells, 3456 wells or 9600 wells. In some examples, each well has a volume in the range of approximately 1 nanoliter (nL) to approximately 100 milliliters (mL), and in some more specific 96-well examples, a total volume in the range of approximately 350 microliter (µL) to approximately 400 µL, and a typical working volume in the range of approximately 25 µL to approximately 340 µL. Although each well is typically of a cylindrical shape having a circular cross-section with an open top end and a closed bottom end, other shapes can be used, for example, square or other rectangular cross-sections are available. Each well is further defined by a bottom surface on which a sample may be deposited. In some examples, the multi-well plate is formed from a plastic material, such as a thermoplastic material such as polystyrene. In some examples, the multi-well plate 308 is formed from a glass material. In some examples, portions of the multi-well plate excluding the bottom surfaces of the wells 309 can further include carbon. For example, for fluorescent biologic assays it is generally desirable that the sides of the wells 309 are black to absorb/block external/ambient light while the bottoms of wells should be clear/transparent to light in the visual wavelengths and fluorescence wavelengths of interest. The sample platform 305 can either be transparent or include a cutout portion below the multi-well plate to enable light to pass from the samples to the lenses of the optical system.

FIG. 3B shows a bottom view of an example illumination system according to some implementations. As described above, the illumination system generally includes a printed circuit board or other dielectric substrate 312 onto or into which array of light sources 322 can be electrically and physically coupled. As described above, the light-emitting portions of the light sources 322 are oriented so as to radiate light toward the lenses of the optical system (and consequently also the samples in the wells of the well plate). As an example, the array of light sources 322 can be implemented with an LED matrix. Each light source 322 can include one or more LEDs. For example, in some implementations, each light source 322 includes a set of three or more LEDs including a red LED, a green LED and a blue LED. In some other implementations, such as that illustrated in FIG. 3B, each light source 322 includes a single LED, and more specifically, a single RGB (Red, Blue, Green) LED including a red sub-LED 324a, a green sub-LED 324b and a blue sub-LED 324c. In other words, each RGB LED actually has 3 semiconductor light sources; one red, one blue and one green. Whether implemented as a set of three distinct red, green and blue LEDs or as a single RGB LED, each light source 322 can be capable of producing any visible color of light by varying the intensities of the red, green and blue light (for example, in response to particular voltage signals provided by the controller). Additionally or alternatively, each light source 322 also can include an LED for generating light in non-visible parts of the spectrum, such as infrared light or ultraviolet light.

In some implementations, each light source 322 occupies a footprint of less than 1 mm by 1 mm. In implementations configured to image 96-well plates, the center to center distance (or "pitch") between each well can by 9 mm while the center to center distance between each light source 322 can be 3 mm. This means that there will be room for three light sources between the centers of adjacent neighboring wells. This arrangement and ratio of LEDs to wells ensures that multiple light sources 322 can illuminate the samples—each at a different angle of incidence. In some example implementations, the number L of distinct light sources 322 that are desired to ensure a sufficient number n of different angles of incidence are obtained for each well can be found according to equation 1 below.

$$L = \left[ (m*R) + 2\left(\frac{(\sqrt{n}-1)}{2} - \frac{m-1}{2}\right)\right] * \left[ (m*C) + 2\left(\frac{(\sqrt{n}-1)}{2} - \frac{m-1}{2}\right)\right] \quad (1)$$

where n is the desired number of angles of incidence and m is a number representative of a scaling factor indicative of a ratio of the density of light sources to the density of wells.

In the illustrated 96-well implementation, where the number of rows R of wells is 8 and the number C of columns of wells is 12, and taking n to be 49 and m to be 3, the number L of light sources 322 is 1120 (for example, 1120 RGB LEDs arranged in 28 rows and 40 columns). In some implementation, the illumination system can further include side-mounted light sources (for example, high power LEDs, not shown) for use in increasing the intensities of the excitation signals for fluorescence imaging scans to, in turn, increase the intensities of the emission signals emitted by the fluorophores within the samples.

Figure 3C:
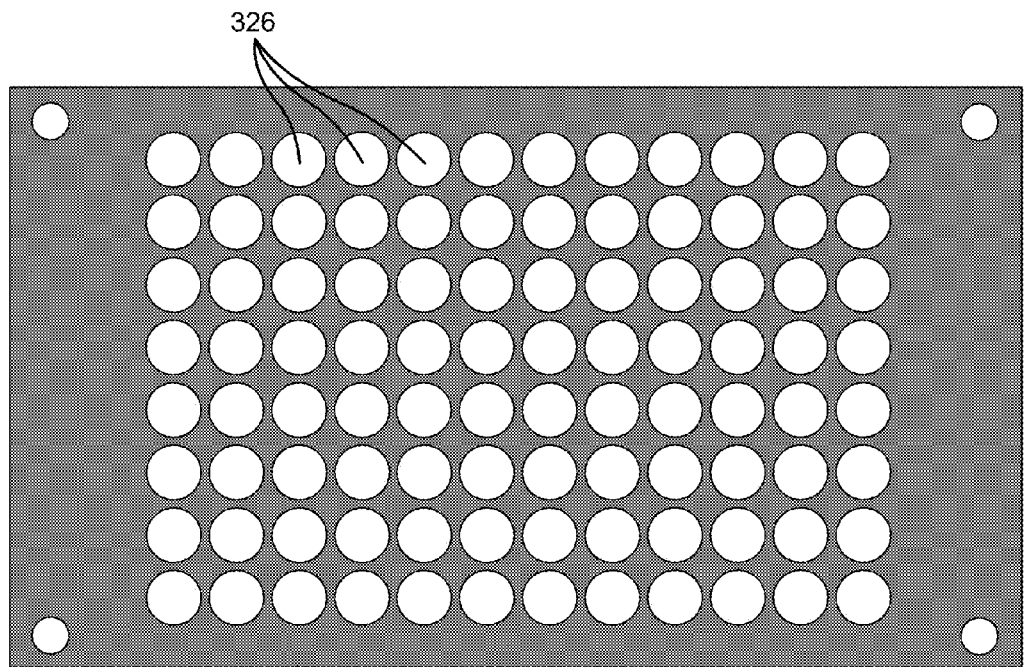
FIG. 3C shows a top view of an example lens array according to some implementations.

FIG. 3C shows a top view of an example lens array 316 according to some implementations. Like the lens arrays of FIG. 2B, the lens array of FIG. 3C includes a substrate including an array of lenses 326. As described above, the optical system includes at least one lens array 316, and in various implementations, at least two (for example, 2, 3, 4 or more) lens arrays in a vertically-aligned (or "stacked") arrangement. As described above, in multi-lens-array implementations, each of the lenses 326 in each lens array 316 is in vertical alignment with a corresponding one of the lenses 326 in each of the other lens arrays 316. The number of lens arrays 316 and the types of the lenses 326 in each of the lens arrays can be optimized for particular applications. Generally, each of the lenses 326 within a given lens array 316 will be identical to all the other lenses within the array, and different than all of the other lenses in the other lens arrays. In some implementations or applications, the combined set of lens aligned and otherwise associated with each well can have a numerical aperture (NA) in the range of approximately 0.05 to approximately 0.6.

FIG. 4A shows a diagram of a portion of an example optical arrangement 400 including three lenses according to some implementations. Generally, the arrangement 400 represents the lenses as aligned and positioned for one well of a multi-well plate. Thus, each of the wells of the multi-well plate would include an identical arrangement 400, with each of the elements of each arrangement being provided at the array level with like elements. In the illustrated representation, the top line 402 of the arrangement 400 represents the location of the sample within the well (on or above the inner bottom surface of the well) while element 404 represents the bottom of the well (between the inner bottom surface of the well and the exterior bottom surface of the well plate). Element 406a represents a first lens element of a first lens array, element 406b represents a second lens element of a second lens array, and element 406c represents a third lens element of a third lens array. The set of lens 406a, 406b and 406c are configured to focus light onto an active surface of a corresponding image sensor 408. The lines passing through the various lenses and other elements in FIG. 4A represent light rays originating from different regions of the sample. In the illustrated implementation, the optical arrangement 400 further includes a portion of an optical filter 410, for example, for use in fluorescence imaging applications to filter light at excitation signal wavelengths. As described above, the optical filter can in various implementation generally be positioned anywhere between the multi-well plate and the imaging system, including between various ones of the lens arrays.

FIG. 4B shows an enlarged view of a diagram of a portion of an example optical arrangement 401 including four lenses according to some implementations. The arrangement 410 is similar to the arrangement 400 shown in FIG. 4A, for example, having a top line 412 representing the location of the sample and an element 414 representing the bottom of the well. However, in the implementation of FIG. 4B, the optical arrangement 410 includes four lenses: element 416a representing a first lens element of a first lens array, element 416b representing a second lens element of a second lens array, element 416c representing a third lens element of a third lens array and element 416d representing a fourth lens element of a fourth lens array. The set of lens 416a, 416b, 416c and 416d are configured to focus light onto an active surface of a corresponding image sensor (not shown). In the illustrated implementation, the optical arrangement 401 also includes a portion of an optical filter 420, for example, for use in fluorescence imaging applications to filter light at excitation signal wavelengths.

Again, the number and types of the lens arrays and corresponding lenses can generally be dependent on the application. As an example, in an implementation in which the imaging system can be used in Green Fluorescent Protein (GFP) imaging, an optical arrangement such as that shown in FIG. 4B is well-suited, for example, providing better results than a three-lens-array arrangement such as that shown in FIG. 4A. Generally, the lens characteristics of each lens may be particularly designed for different wavelengths.

Referring back to FIG. 3C, in some implementations, each lens array 316 is formed of one integral piece of material. For example, the lens array 316 can be formed through an injection molding or three-dimensional (3D) printing process. Traditionally, such lenses would not have sufficiently low geometric aberrations to enable high resolution imaging of a relatively wide field of view at the scale need to image a large number of wells simultaneously in parallel. However, the use of multiple lens arrays, and thus multiple lenses for each well, can at least partially negate the effects of geometrical aberrations. Generally, the more lenses that are used for each well, the more geometrical aberrations in those lenses can be canceled out. Additionally, FP techniques as described herein can be used to further correct for any aberrations or to remove other image artifacts enabling the reconstruction of a high resolution image.

In implementations designed for fluorescence imaging applications, the optical system also includes an optical filter 220 located between the bottom surface of the multi-well plate 208 and the image sensor system. The optical filter 220 blocks excitation light from the illumination system (as well as any other light not emitted by the fluorophores in the samples within the multi-well plate) from striking the image sensors 219 of the image sensor system. Continuing the example above, for GFP imaging, the optical filter should be a green filter, that is, a filter passing wavelengths of light in a green portion of the visible spectrum. The excitation signal light should be higher energy light, and in particular applications, blue light. This is because the green fluorescent proteins absorb light in the blue portion of the spectrum and emit light in the green portion of the spectrum. The green filter then enables the emitted light to pass through to the image sensors while blocking the excitation light. In some implementations, the excitation light also can be turned off immediately before acquiring the image data.

In some implementations or applications, the range of wavelengths of the bright field illumination for the FP imaging fall within the passband of the optical filter 220 so that the optical filter passes light from the light sources 322 that passes through the samples in the wells. In such instances, the image sensors can acquire a sequence of uniquely illuminated bright field images while leaving the filter 220 in place. Continuing with the example above, bright field FP imaging of the GFP samples can be performed with green light. In some other instances, the range of wavelengths of the bright field illumination from the light sources 322 do not fall within the passband of the optical filter 220. In other words, in instances in which it is necessary or desirable to keep the optical filter within the imaging system during the FP imaging, the bright field FP imaging should be performed using light of the same or similar color as the filter used in the fluorescent imaging, else the filter should be removed during the FP image acquisition process. In some implementations, the optical filter can be readily removable and/or replaceable with one or more different optical filters capable of filtering and passing different wavelengths of light. For example, the optical filter 220 can be inserted into another aperture slot in the enclosure 202. In such implementations, the bright field FPM imaging can be performed with light of a different color or with white light.

In some implementations, the optical filter is fabricated from a glass or plastic material and is in the shape of a rectangular solid having a width (along the x axis) and a length (along a y axis) sufficiently large to provide filtering for all of the light scattered or emitted by the samples and incident on the lenses of the optical system. In single-channel fluorescence imaging applications, a single band or low pass filter can be used; for multi-channel fluorescence imaging applications, a multi band filter can be used. As described above, because the optical filter 220 does not affect the path of the light, the optical filter 220 can be positioned anywhere between the bottom surface of the multi-well plate 208 and the image sensors 209 of the image sensor system.

Figure 3D:
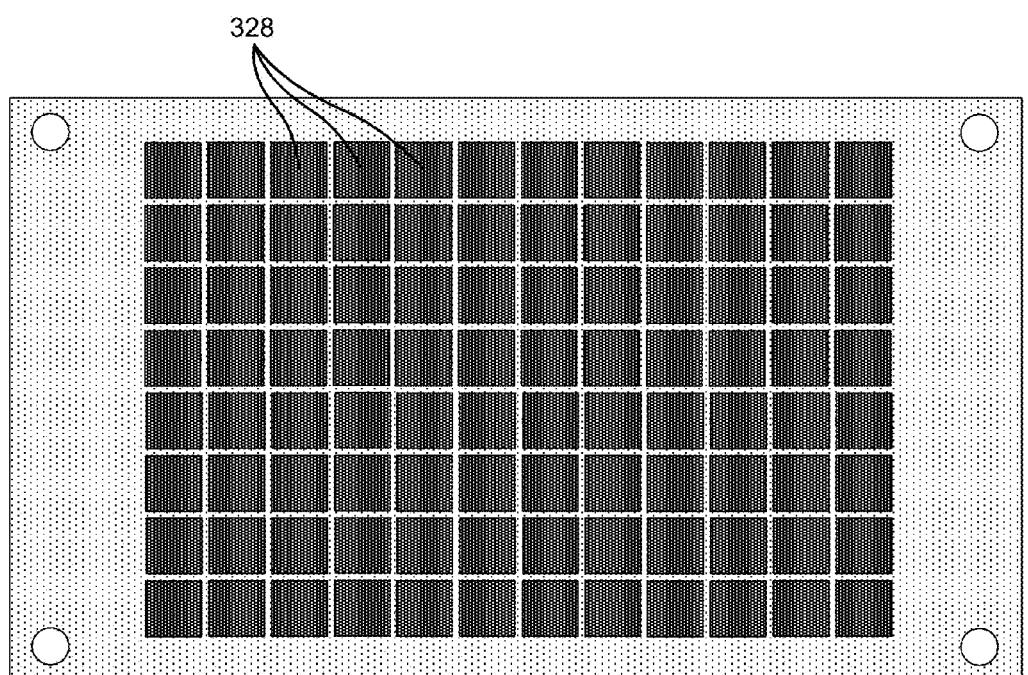
FIG. 3D shows a top view of an example image sensor system according to some implementations.

FIG. 3D shows a top view of an example image sensor system according to some implementations. Like the image sensor system of FIG. 2B, the image sensor system of FIG. 3D includes a circuit board or other dielectric substrate 318 onto which an array of T image sensors 328 arranged in R rows and C columns can be electrically and physically coupled. In some implementations, each of the image sensors 328 has a field of view (FOV) of the respective sample well in the range of 0.5 mm to 6 mm in diameter, and in one specification example implementation, an FOV of 1 mm diameter. In some implementations, each of the image sensors 328 also is capable of capturing raw images at a spatial resolution of 0.5 μm to 5 μm (prior to subsequent FP processing). As described above, the active light-sensitive regions of the image sensors 328 can be oriented away from a first or upper surface of the circuit board 318 toward the lenses of the optical system while the conductive leads of the image sensors 328 can be electrically coupled with the controller 210 via conductive traces printed or otherwise deposited on a second or lower surface of the circuit board 318 and via a communication interface (for example, a Universal Serial Bus (USB) interface) that is connected with the controller 210. In some implementations, each of the image sensors is an active-pixel sensor (APS) device such as CMOS-based APS cameras.

In some implementations, the raw image data captured by each of the image sensors is transferred to the controller 210 through a high speed data transfer channel (for example, at a data rate greater than 5 Gb/s). In some implementations, the image sensor system further includes a liquid cooling system that circulates cooling liquid around the surfaces surrounding the image sensors.

III. Variable-Illumination Fourier Ptychographic Imaging Methods

As described above, the imaging systems 100 and 200 are capable of FP image acquisition of each and all of the sample wells of an entire multi-well plate in parallel. In particular implementations, the imaging systems 100 and 200 also are capable of fluorescence image acquisition of each and all of the sample wells of an entire multi-well plate in parallel. An image acquisition (sample) time refers to a time during the exposure duration of each of the image sensors during which each of the image sensors measures a light intensity distribution to capture an intensity image for a respective well of the multi-well plate. The FP imaging process typically comprises a raw image acquisition (data collection) phase (or "process") and an FP reconstruction phase (or "process"). During the FP image acquisition process, the controller causes the illumination system to turn on particular subsets or patterns of the light sources. For example, the FP image acquisition process can include a plurality of scanning operations (or "scans"), each of which scans includes a respective image acquisition by each of the image sensors in the image sensor system. Each of the scans is associated with a different pattern of illumination of the light sources. Throughout the course of the entire FP image acquisition process, each of the image sensors in the array of image sensors acquires s intensity bright field images (corresponding to s scans) while the light sources of the illumination system provide plane wave illumination of each of the wells from n different (unique) respective illumination angles of incidence. During each scan, each image sensor acquires an image based on a particular illumination pattern of the light sources. Generally, the number s of scans can be equal to the number n of unique illumination incident angles desired for each well. In this way, assuming a fixed value of n, the number of scans is independent of the number T of wells in the multi-well plate.

Figure 5:
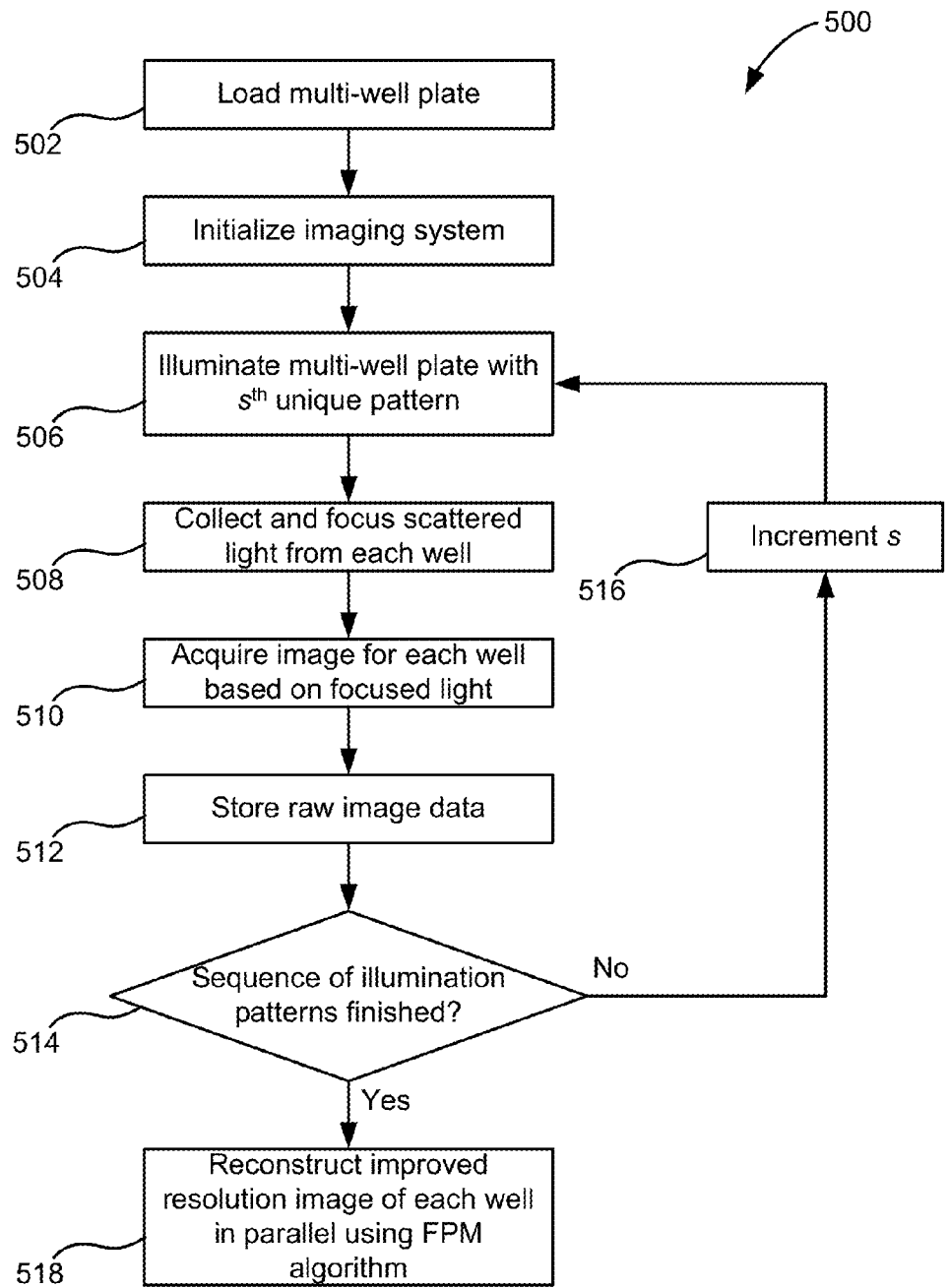
FIG. 5 shows a flowchart illustrating an example FP imaging process for imaging a multi-well plate according to some implementations.

FIG. 5 shows a flowchart illustrating an example FP imaging process 500 for imaging a multi-well plate according to some implementations. For example, the process 500 can be performed using the systems, devices and arrangements described above with respect to FIGS. 1-4. In some implementations, the controller 110 is configured perform one or more operations of the FP imaging process 500. In some implementations, the FP process 500 begins in operation 502 with loading a multi-well plate into the imaging system. In operation 504, the controller initializes the illumination system and the image sensor system. Initializing the illumination system in operation 504 can include retrieving illumination pattern information from a non-volatile memory and loading the retrieved illumination pattern information into a volatile memory for subsequent use in performing a series of sequential scanning operations. Initializing the image sensor system in operation 504 can include powering on or otherwise preparing the image sensors to receive light and to generate image data. In some implementations, initializing the illumination system and the image sensor system in operation 504 also can include a calibration operation to determine the actual values of the angles of incidence that will illuminate each of the wells.

After initialization, the controller performs an $s^{th}$ scan (where s is an integer between 1 and n, inclusive, and where n is the number of angles of incidence). As described above, during each scan, the controller causes the illumination system to produce a unique pattern of illumination and causes the image sensor system to capture/acquire an image for each of the wells. In some implementations, each scan can be performed or conceptualized as a sequence of sub-operations. For example, each scan can include a sequence of operations 506, 508, 510 (and in some cases 512). In block 506, the controller causes the illumination system to illuminate the multi-well plate with an $s^{th}$ unique illumination pattern.

Figure 6A:
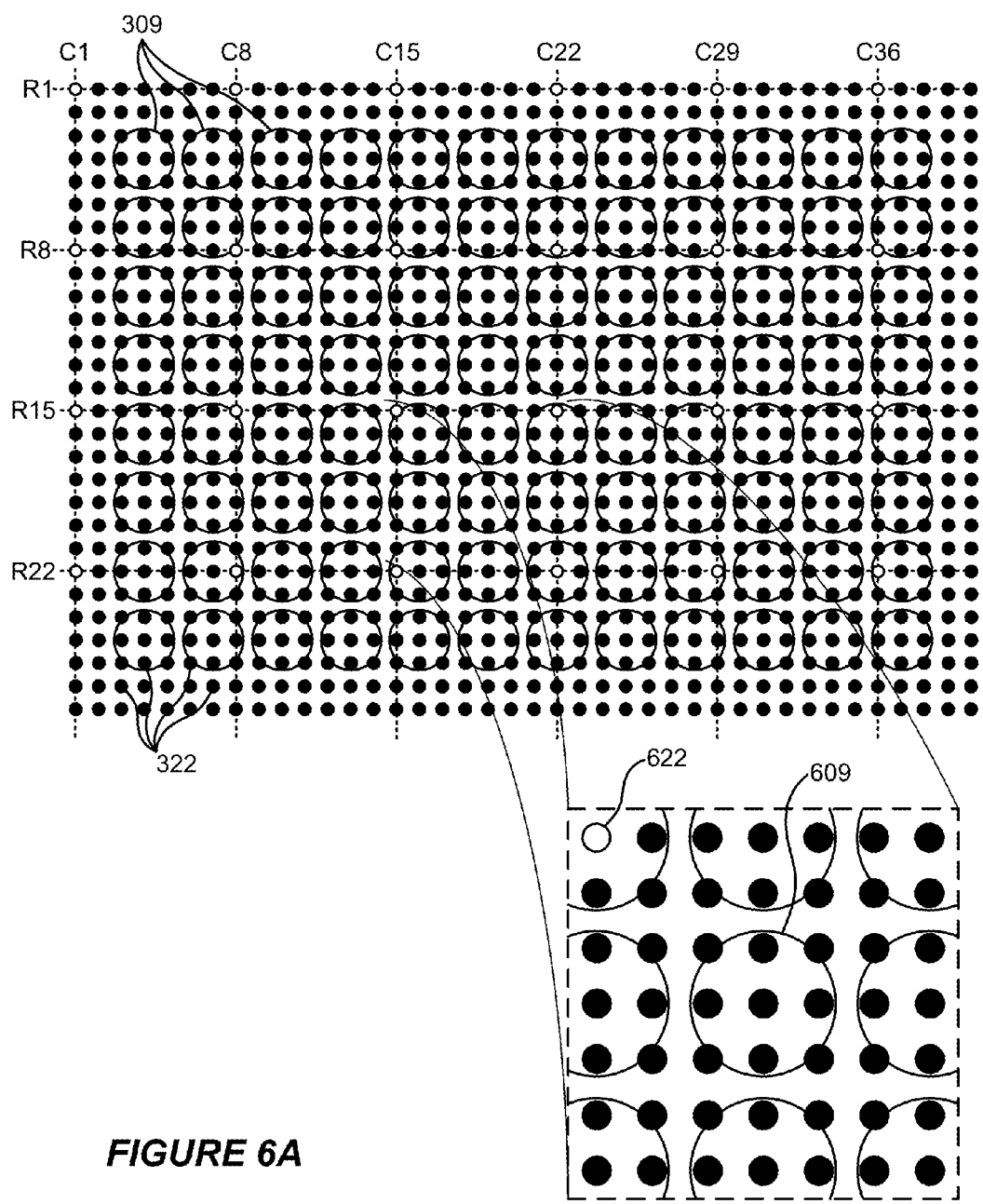
FIG. 6A shows a diagram of an example arrangement of light sources and wells illuminated according to a first illumination pattern during a first scan according to some implementations.

FIG. 6A shows a diagram of an example arrangement of light sources 322 and wells 309 illuminated according to a first illumination pattern during a first scan according to some implementations. In the illustrated implementation, the first illumination pattern is configured or otherwise suited for a 96-well plate. As shown, while each well 309 can be illuminated by multiple respective ones of the light sources 322, in the illustrated implementation, only the light sources 322 positioned at the intersections of the $1^{st}$, $8^{th}$, $15^{th}$ and $22^{nd}$ rows and the $1^{st}$, $8^{th}$, $15^{th}$, $22^{nd}$, $29^{th}$ and $36^{th}$ columns are illuminated in the first illumination pattern during the first scan. As such only 24 of the light sources 322 are turned on during the first scan in the illustrated 96-well implementation (these light sources are shown as white circles while the light sources that are not on are shown as all black). As a consequence, in the illustrated implementation, only one of the light sources that can illuminate a particular well actually illuminates the well in each scan. For example, FIG. 6A also shows an enlarged close-up view of a portion of the arrangement showing only those light sources 322 (49 in the illustrated implementation) that can illuminate a given well 609. As shown, only one of the possible light sources 622 actually illuminates the well during each scan. In some implementations, the illumination pattern changes sequentially in a raster-like pattern as the scans continue throughout the series of image acquisitions during the image acquisition phase.

Figure 6B:
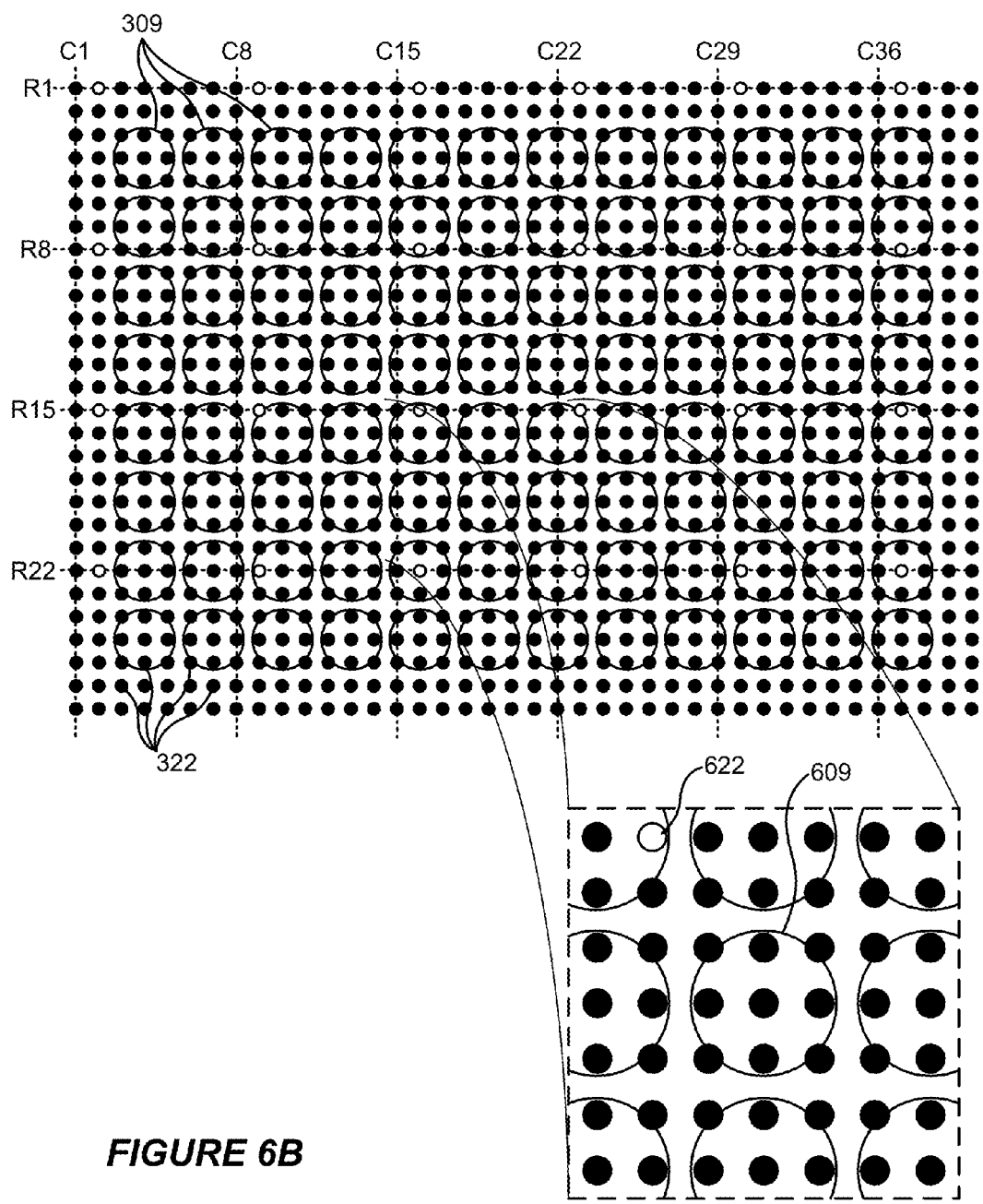
FIG. 6B shows the arrangement of FIG. 6A illuminated according to a $2^{nd}$ illumination pattern during a $2^{nd}$ scan.
Figure 6C:
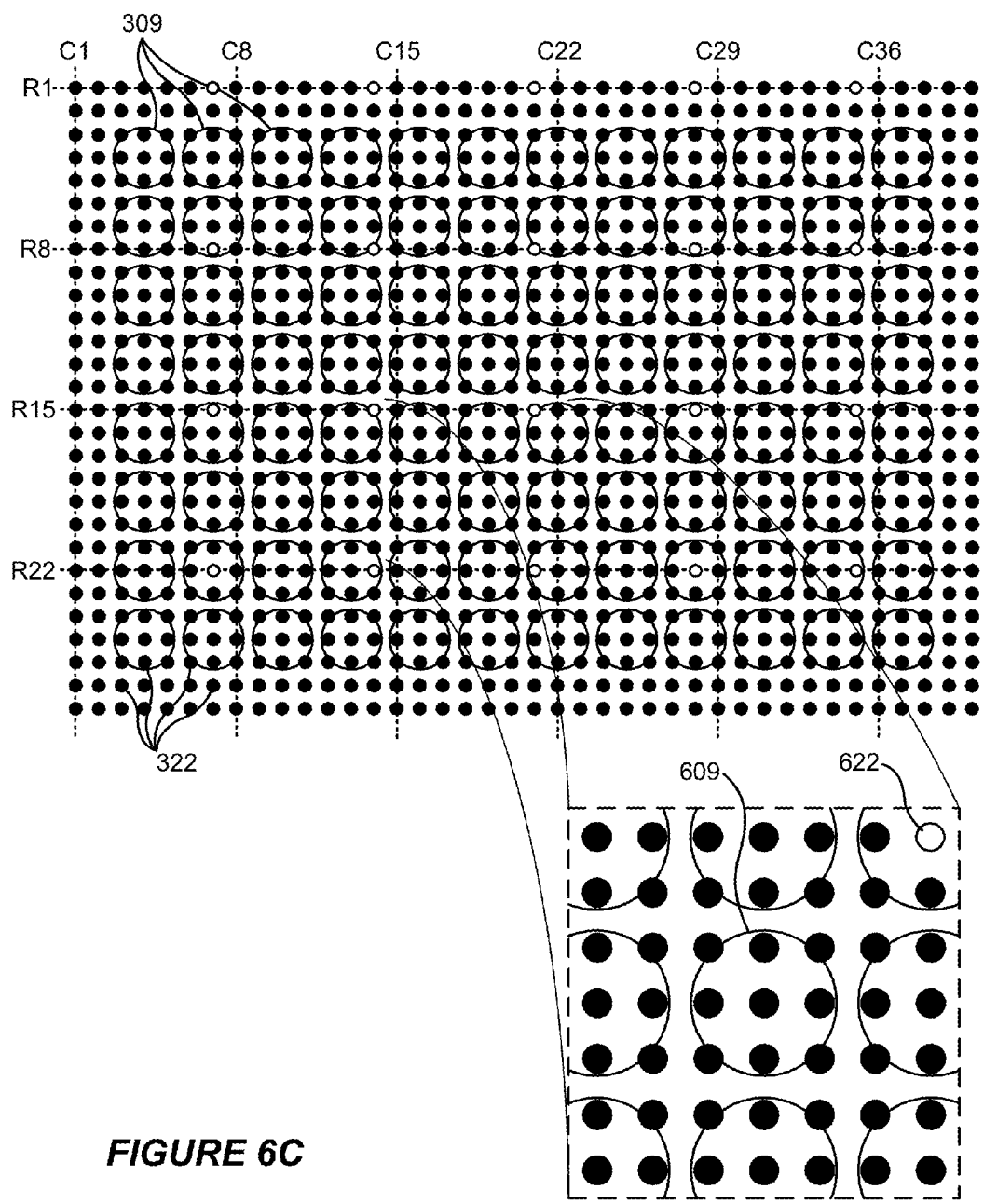
FIG. 6C shows the arrangement of FIG. 6A illuminated according to a $7^{th}$ illumination pattern during a $7^{th}$ scan.
Figure 6D:
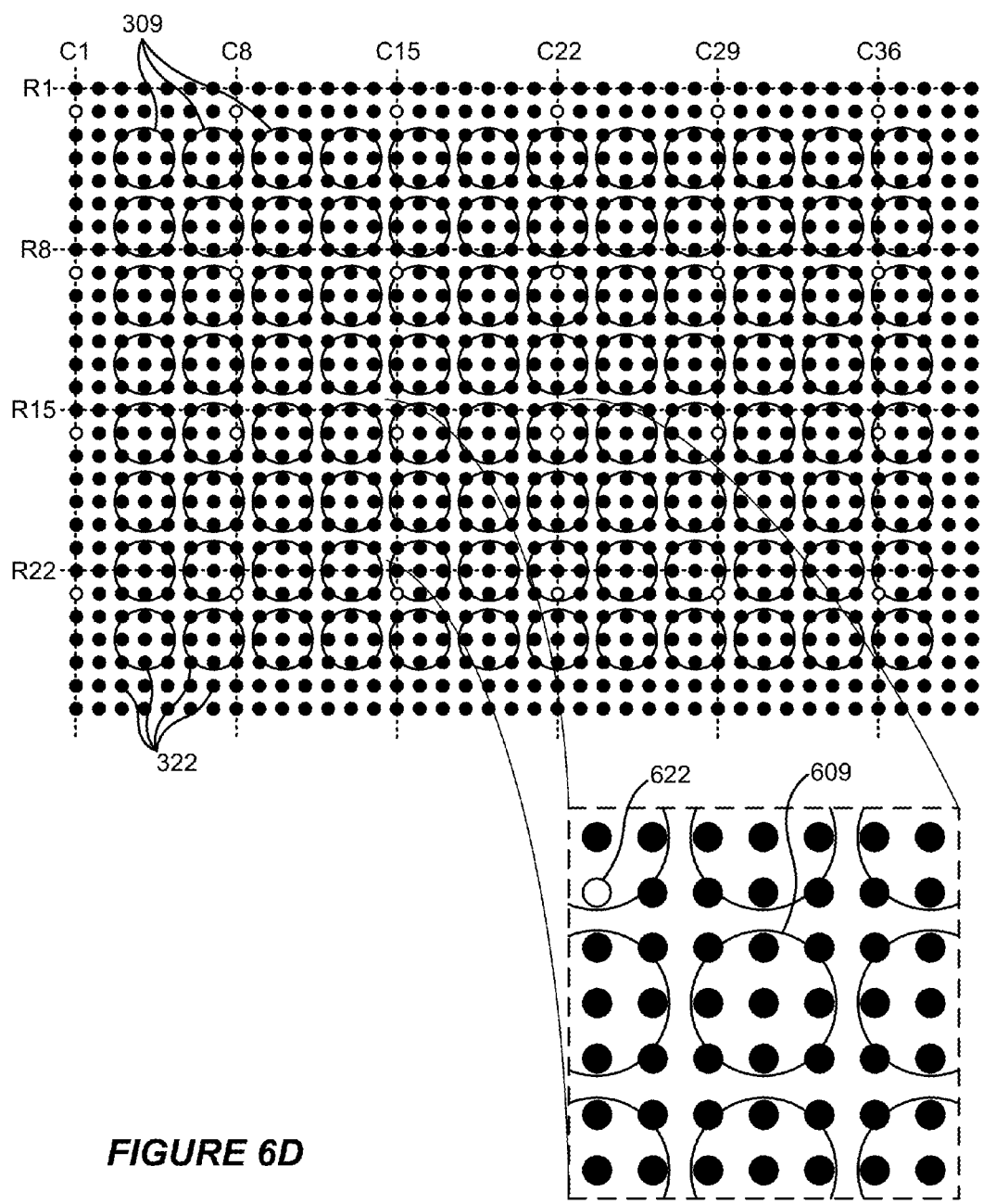
FIG. 6D shows the arrangement of FIG. 6A illuminated according to an $8^{th}$ illumination pattern during a $8^{th}$ scan.
Figure 6E:
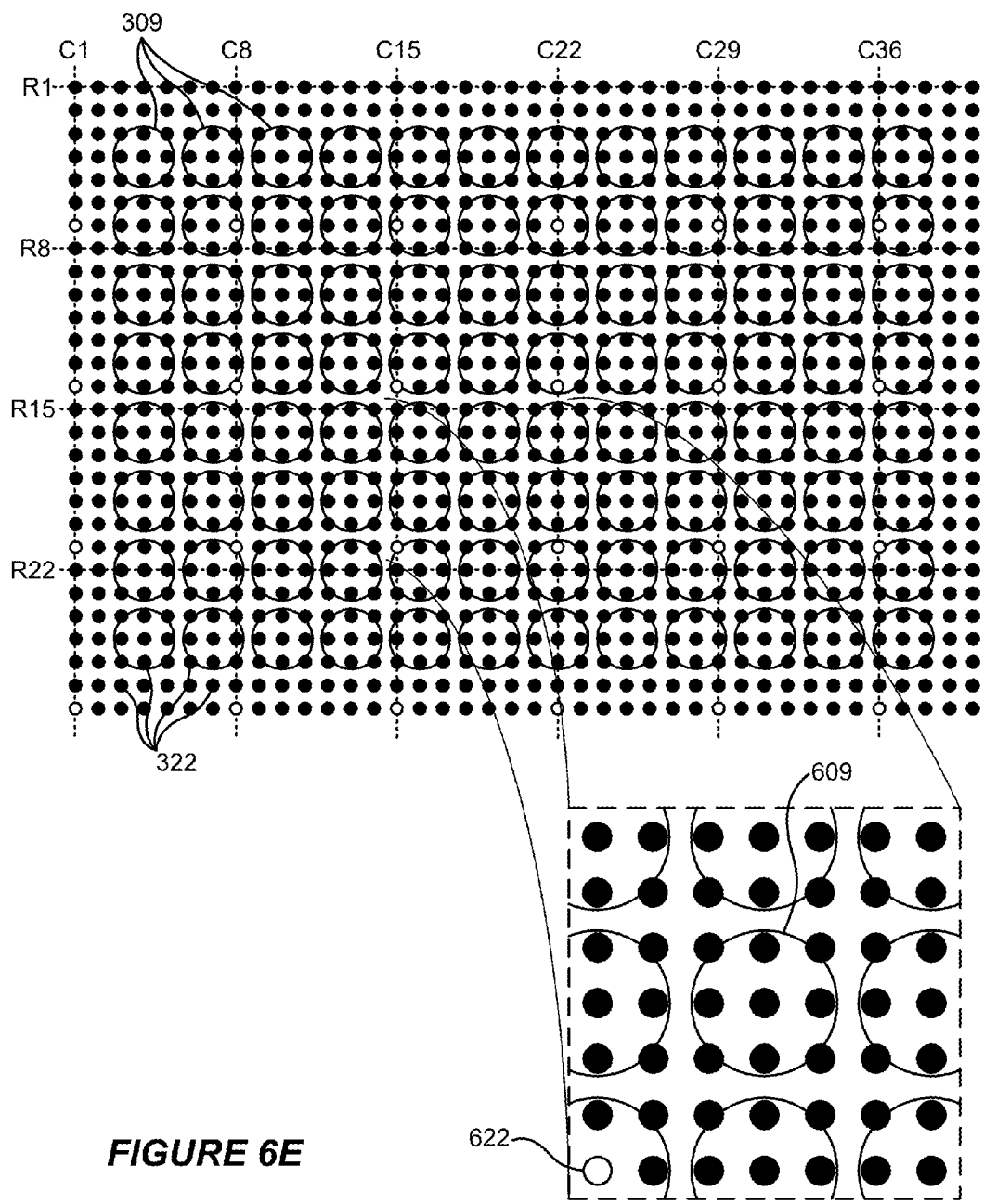
FIG. 6E shows the arrangement of FIG. 6A illuminated according to a $42^{nd}$ illumination pattern during a $42^{nd}$ scan.
Figure 6F:
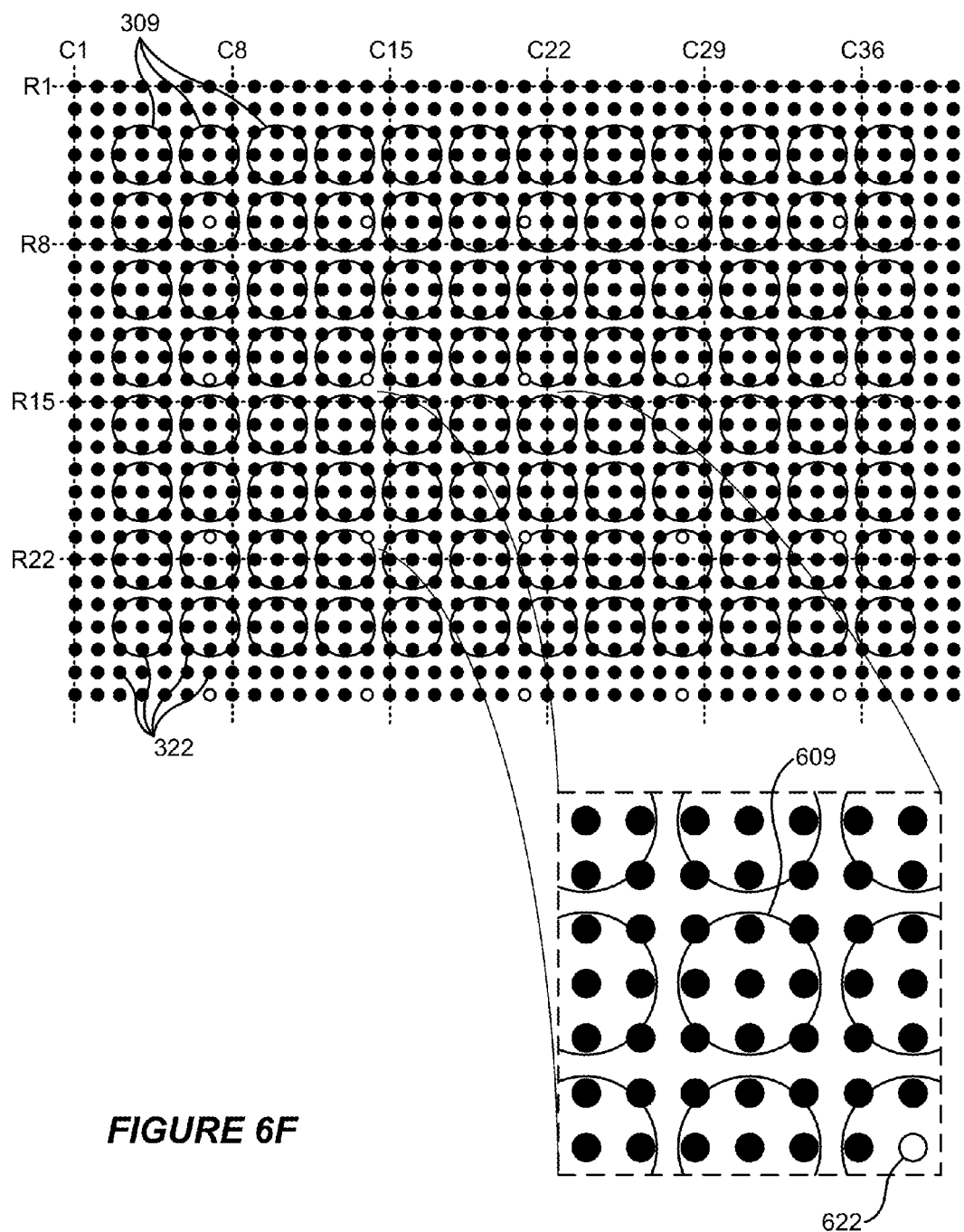
FIG. 6F shows the arrangement of FIG. 6A illuminated according to a $49^{th}$ illumination pattern during a $49^{th}$ scan.

For example, FIG. 6B shows the arrangement of FIG. 6A illuminated according to a second illumination pattern during a second scan. In the second illumination pattern, only the light sources 322 positioned at the intersections of the $1^{st}$, $8^{th}$, $15^{th}$ and $22^{nd}$ rows and the $2^{nd}$, $9^{th}$, $16^{th}$, $23^{rd}$ and $30^{th}$ columns are illuminated. In such an implementation, the illumination pattern shifts by one column to the right during each successive scan until the $7^{th}$ column is illuminated, at which point the illumination pattern shifts down to the next row and back to the first column for the next scan. The process then repeats until the $7^{th}$ column of the $7^{th}$ row is reached in the $n^{th}$ ($49^{th}$) scan. By way of illustration, FIG. 6C shows the arrangement of FIG. 6A illuminated according to a $7^{th}$ illumination pattern during a $7^{th}$ scan. In the $7^{th}$ illumination pattern, only the light sources 322 positioned at the intersections of the $1^{st}$, $8^{th}$, $15^{th}$ and $22^{nd}$ rows and the $7^{th}$, $14^{th}$, $21^{st}$, $28^{th}$ and $35^{th}$ columns are illuminated. FIG. 6D shows the arrangement of FIG. 6A illuminated according to an $8^{th}$ illumination pattern during an $8^{th}$ scan. In the $8^{th}$ illumination pattern, only the light sources 322 positioned at the intersections of the $2^{nd}$, $9^{th}$, $16^{th}$ and $23^{rd}$ rows and the $1^{st}$, $8^{th}$, $15^{th}$, $22^{nd}$, $29^{th}$ and $36^{th}$ columns are illuminated. FIG. 6E shows the arrangement of FIG. 6A illuminated according to a $42^{nd}$ illumination pattern during a $42^{nd}$ scan. In the $42^{nd}$ illumination pattern, only the light sources 322 positioned at the intersections of the $7^{th}$, $14^{th}$ and $21^{st}$ rows and the $1^{st}$, $8^{th}$, $15^{th}$, $22^{nd}$, $29^{th}$ and $36^{th}$ columns are illuminated. Finally, FIG. 6F shows the arrangement of FIG. 6A illuminated according to a $49^{th}$ illumination pattern during a $49^{th}$ scan. In the $49^{th}$ illumination pattern, only the light sources 322 positioned at the intersections of the $7^{th}$ $14^{th}$ and $21^{st}$ rows and the $7^{th}$, $14^{th}$, $21^{st}$, $28^{th}$ and $35^{th}$ columns are illuminated.

The lenses of the optical system receive (or "collect") light scattered by or otherwise issuing from the respective samples during each scan and focus the received light onto the image sensors of the image sensor system. Although the reception and focusing of the light during each scan is generally performed by passive elements (the lenses of the optical system), this portion of the path of the light is still referred to as operation 508. In operation 510, each of the image sensors receives light focused by a corresponding lens (or set of lenses) of the optical system acquires image data based on the focused light. In operation 512, the image data may be stored in one or both of a volatile memory quickly accessible by a processor of the controller or a non-volatile memory for longer term storage. As described above, the image data represents an intensity distribution obtained during an exposure time of the scan (the image data acquired by a particular image sensor during a particular scan is referred to as an "image frame" or simply an "image"). In some implementations, each of the scans takes less than approximately 1 ms, enabling all n scans for an entire multi-well plate to be completed in less than 1 second.

In some implementations, a multiplexing approach can be used to further decrease the total scan time—the time required to obtain image data for n incidence angles. In one multiplexing embodiment, multiple light sources around each well can be turned on at the same time in a unique pattern during the capture of each raw image of each well. Using a multiplexing process, intensity data associated with each illumination angle can be separated from the raw image captured. In this way, fewer than n scans are required for each of the wells. An example of a multiplexing process can be found in U.S. patent application Ser. No. 14/960,252 titled "MULTIPLEXED FOURIER PTYCHOGRAPHY IMAGING SYSTEMS AND METHODS" filed on Dec. 4, 2015, which is hereby incorporated by reference in its entirety.

In operation 514, a processor (for example, of the controller) determines whether all n of the scans have been completed. If there are remaining scans to be completed, s is incrementally updated in operation 516 so that the next scan (the $(s+1)^{th}$) scan is then performed using the next (the $(s+1)^{th}$) illumination pattern. When all of the scans are complete, a processor (for example, of the controller) performs a parallel reconstruction process to reconstruct (or "generate") an improved (higher) resolution image of each sample in parallel in operation 518. During the FP reconstruction process, the n intensity images for each sample well are iteratively combined in the Fourier domain to generate higher-resolution image data. At each iteration, a filter is applied in the Fourier domain for a particular plane wave incidence angle, an inverse Fourier transform is applied to generate a lower resolution image, the intensity of the lower resolution image is replaced with an intensity measurement, a Fourier transform is applied, and the corresponding region in Fourier space is updated. Generally, the reconstruction process includes a phase retrieval technique that uses angular diversity to recover complex sample images. The recovery process alternates enforcement of known image data acquired in the spatial domain and a fixed constraint in the Fourier domain. This phase retrieval recovery can be implemented using, for example, an alternating projections procedure, a convex reformulation of the problem, or any non-convex variant in-between. Instead of needing to translate a sample laterally by mechanical means, the reconstruction process varies the spectrum constraint in the Fourier domain to expand the Fourier passband beyond that of a single captured image to recover a higher-resolution sample image.

Figure 7:
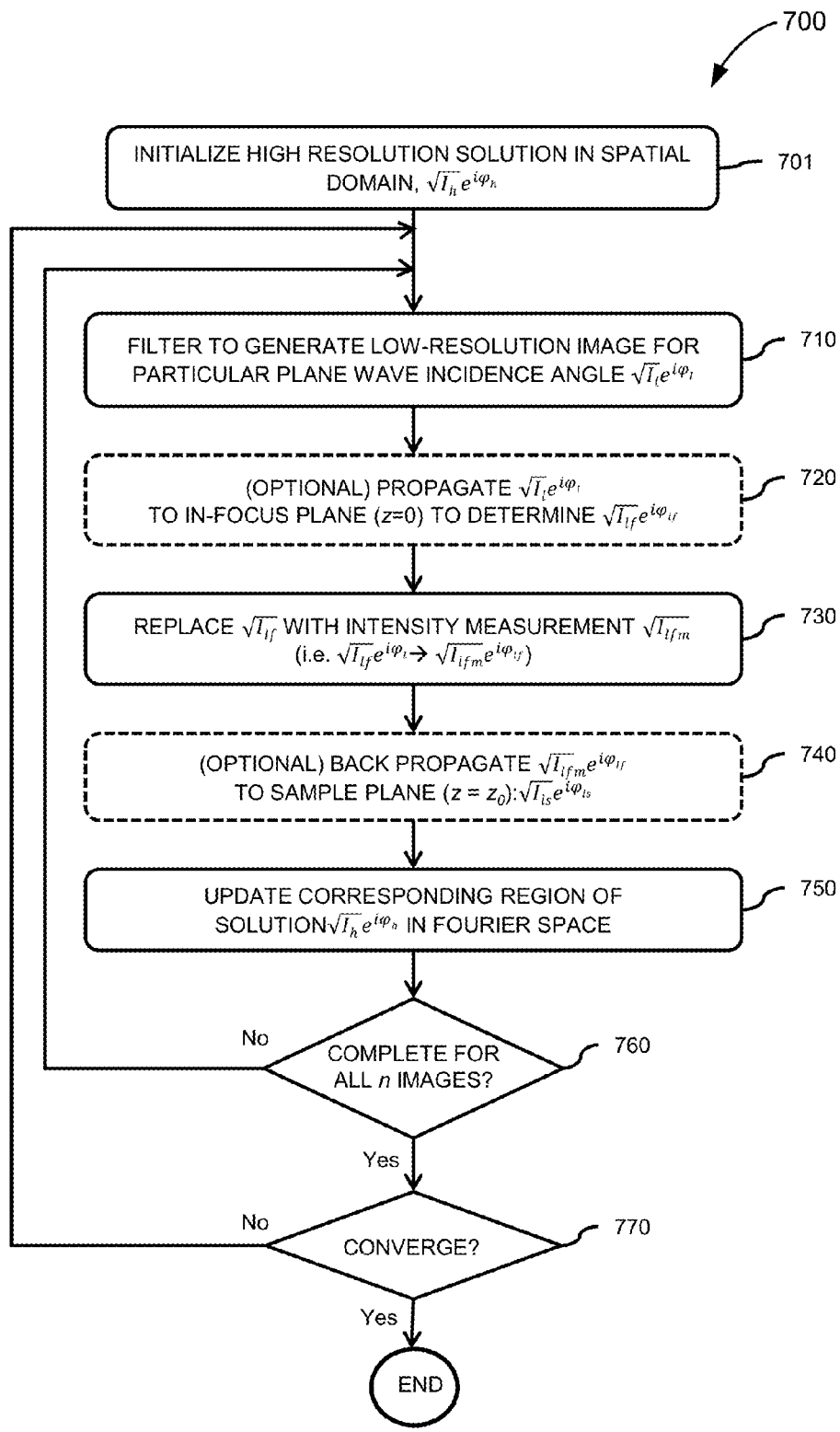
FIG. 7 shows a flowchart of an example FP reconstruction process according to some implementations.

Two examples of FP reconstruction processes are discussed in detail with respect to FIGS. 7 and 8 below. In some implementations, the controller then causes a display to display the reconstructed images for each of the wells. FIG. 7 shows a flowchart of an example FP reconstruction process 700 (also referred to as an "algorithm") according to some implementations. In some implementations, the controller 110 is configured perform one or more operations of the FP reconstruction process 700. Using this FP reconstruction process, an improved resolution image of each of the samples in each of the sample wells is reconstructed from n low-resolution intensity distribution measurements obtained for each sample, $I_{lm}(k_x^i, k_y^i)$ (indexed by their illumination wavevector, $k_x^i$, $k_y^i$, with i=1, 2 . . . n), such as the n raw intensity images acquired during operations 506, 508 and 510 of the process 500 illustrated in and described with reference to FIG. 5.

In some implementations, the FP reconstruction process 700 begins in operation 701 with initializing a high-resolution image solution $\sqrt{I_h}e^{i\Phi_h}$ in the spatial domain. A Fourier transform is applied to obtain an initialized Fourier transformed image $\tilde{I}_h$. In some implementations, the initial high-resolution solution is determined based on the assumption that the sample is located at an out-of-focus plane $z=z_0$. In some other implementations, the initial solution is determined using a random complex matrix (for both intensity and phase). In some implementations, the initial solution is determined using an interpolation of the low-resolution intensity measurement with a random phase. In some implementations, an example of an initial solution uses $\phi=0$ and uses $I_h$ interpolated from any low-resolution image of the sample area. In some implementations, an example of an initial solution uses a constant value. Regardless, the Fourier transform of the initial solution can be a broad spectrum in the Fourier domain.

In the iterative operations 710, 720, 730, 740, 750, 760 and 770 described below, the high-resolution image of each sample is reconstructed by iteratively combining low-resolution intensity measurements in Fourier space. In some implementations, operations 720 and 740 may be performed if the sample is out-of-focus by the amount of $z_0$.

At 710, the processor performs low-pass filtering of the high-resolution image $\sqrt{I_h}e^{i\Phi_h}$ in the Fourier domain to generate a low-resolution image $\sqrt{I_l}e^{i\Phi_l}$ for a particular plane wave incidence angle $(\theta_x^i, \theta_y^i)$ with a wave vector $(k_x^i, k_y^i)$. The Fourier transform of the high-resolution image is $\tilde{I}_h$ and the Fourier transform of the low-resolution image for a particular plane wave incidence angle is $\tilde{I}_l$. In the Fourier domain, the reconstruction process filters a low-pass region from the spectrum $\tilde{I}_h$ of the high-resolution image $\sqrt{I_h}e^{i\varphi_h}$. The low-pass region is a circular aperture with a radius of $NA*k_0$, where $k_0$ equals $2\pi/\lambda$ (the wave number in vacuum), given by the coherent transfer function of the first objective lens of the IRI system. In Fourier space, the location of the region corresponds to the illumination angle during the current iteration. For an oblique plane wave incidence with a wave vector $(k_x^i, k_y^i)$, the region is centered about a position $(-k_x^i, -k_y^i)$ in the Fourier domain of $\sqrt{I_h}e^{i\varphi_h}$.

At optional operation 720, using the processor, the low-resolution image, $\sqrt{I_l}e^{i\varphi_l}$ is propagated in the Fourier domain to the in-focus plane at $z=0$ to determine the low-resolution image at the focused position: $\sqrt{I_{lf}}e^{i\varphi_{lf}}$. In one embodiment, operation 720 is performed by Fourier transforming the low-resolution image $\sqrt{I_l}e^{i\varphi_l}$, multiplying by a phase factor in the Fourier domain, and inverse Fourier transforming to obtain $\sqrt{I_{lf}}e^{i\varphi_{lf}}$. In another embodiment, operation 720 is performed by the mathematically equivalent operation of convolving the low-resolution image $\sqrt{I_l}e^{i\varphi_l}$ with the point-spread-function for the defocus. In another embodiment, operation 720 is performed as an optional sub-operation of operation 710 by multiplying $\tilde{I}_l$ by a phase factor in the Fourier domain before performing the inverse Fourier transform to produce $\sqrt{I_{lf}}e^{i\varphi_{lf}}$. Optional operation 720 generally need not be included if the sample is located at the in-focus plane ($z=0$).

At operation 730, using the processor, the computed amplitude component $\sqrt{I_{lf}}$ of the low-resolution image at the in-focus plane, $\sqrt{I_{lf}}e^{i\varphi_{lf}}$, is replaced with the square root of the low-resolution intensity measurement $\sqrt{I_{lfm}}$ measured by the light detector of the IRI system. This forms an updated low resolution target: $\sqrt{I_{lfm}}e^{i\varphi_{lf}}$.

At optional operation 740, using the processor, the updated low-resolution image $\sqrt{I_{lfm}}e^{i\varphi_{lf}}$ may be back-propagated to the sample plane ($z=z_0$) to determine $\sqrt{I_{ls}}e^{i\varphi_{ls}}$. Optional operation 740 need not be included if the sample is located at the in-focus plane, that is, where $z_0=0$. In one embodiment, operation 740 is performed by taking the Fourier transform of the updated low-resolution image $\sqrt{I_{lfm}}e^{i\varphi_{lf}}$ and multiplying in the Fourier space by a phase factor, and then inverse Fourier transforming it. In another embodiment, operation 740 is performed by convolving the updated low-resolution image $\sqrt{I_{lfm}}e^{i\varphi_{lf}}$ with the point-spread-function of the defocus. In another embodiment, operation 740 is performed as a sub-operation of operation 750 by multiplying by a phase factor after performing the Fourier transform onto the updated target image.

At operation 750, using the processor, a Fourier transform is applied to the updated target image propagated to the sample plane: $\sqrt{I_{ls}}e^{i\varphi_{ls}}$, and this data is updated in the corresponding region of high-resolution solution $\sqrt{I_h}e^{i\varphi_h}$ in the Fourier space corresponding to the corresponding to the incidence wave vector $(k_x^i, k_y^i)$. At operation 760, the processor determines whether operations 710 through 760 have been completed for all n uniquely illuminated low resolution intensity images. If operations 710 through 760 have not been completed for all the images, operations 710 through 760 are repeated for the next image.

At operation 770, the processor determines whether the high-resolution solution has converged. In one example, the processor determines whether the high-resolution solution converged to a self-consistent solution. In one case, the processor compares the previous high-resolution solution of the previous iteration or initial guess to the present high-resolution solution, and if the difference is less than a certain value, the solution is determined to have converged to a self-consistent solution. If the processor determines that the solution has not converged at operation 770, then operations 710 through 760 are repeated. In one embodiment, operations 710 through 760 are repeated once. In other embodiments, operations 710 through 760 are repeated twice or more. If the solution has converged, the processor transforms the converged solution in Fourier space to the spatial domain to recover the improved resolution image $\sqrt{I_h}e^{i\varphi_h}$ and the FP reconstruction process ends.

Figure 8:
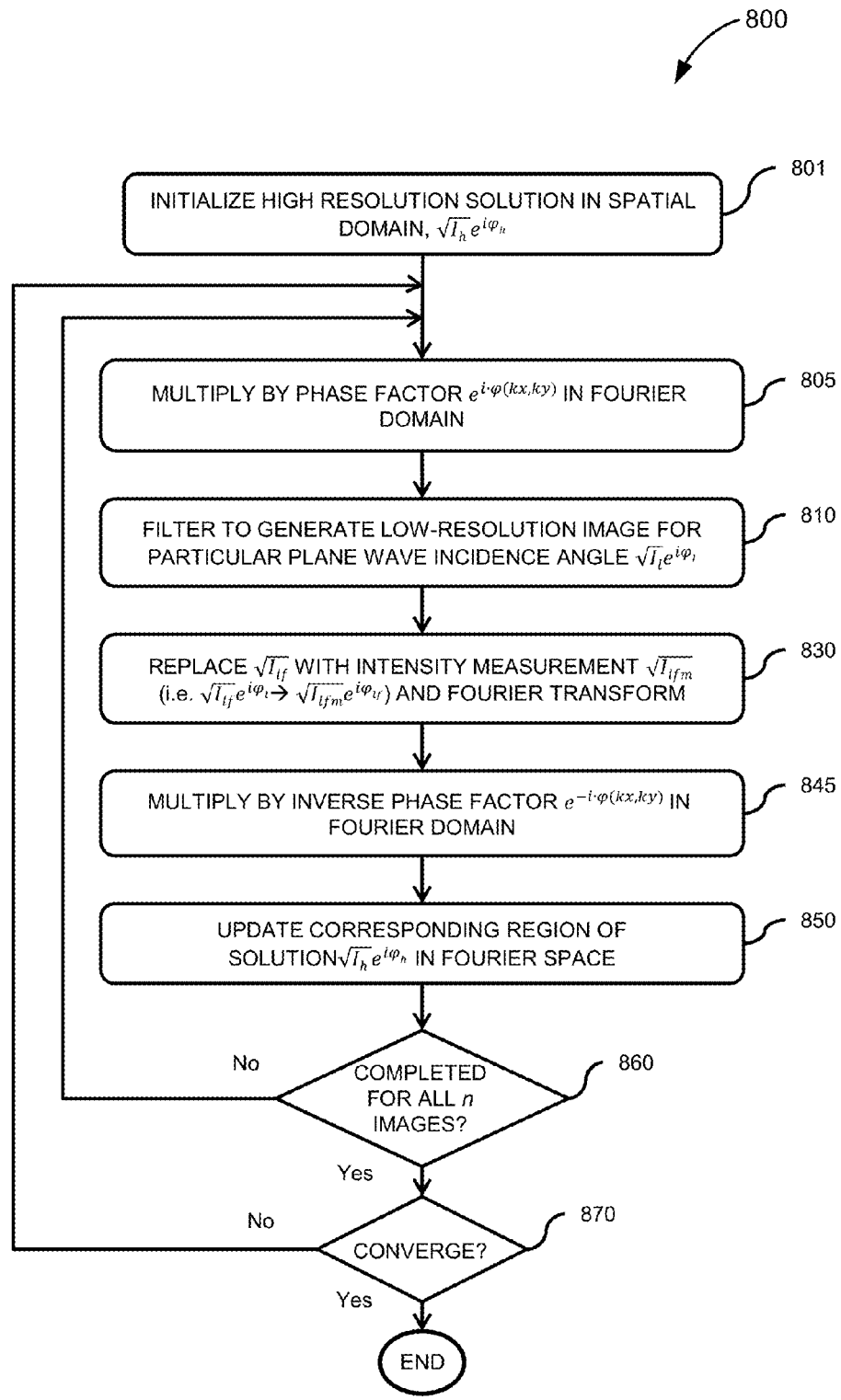
FIG. 8 shows a flowchart of another example FP reconstruction process according to some implementations.

FIG. 8 shows a flowchart of another example FP reconstruction process 800 (also referred to as an "algorithm") according to some implementations. In some implementations, the controller 110 is configured perform one or more operations of the FP reconstruction process 800. Using this FP reconstruction process, an improved resolution image of each of the samples in each of the sample wells is reconstructed from n low-resolution intensity distribution measurements obtained for each sample, $I_{lm}(k_x^i, k_y^i)$ (indexed by their illumination wavevector, $k_x^i$, $k_y^i$, with $i=1, 2 \ldots n$), such as the n raw intensity images acquired during operations 506, 508 and 510 of the process 500 illustrated in and described with reference to FIG. 5.

In this example, the FP reconstruction process includes digital wavefront correction. The FP reconstruction process incorporates digital wavefront compensation in the two multiplication operations 805 and 845. Specifically, operation 805 models the connection between the actual sample profile and the captured intensity data (with includes aberrations) through multiplication with a pupil function: $e^{i\cdot\varphi(k_x,k_y)}$ by the processor. Operation 845 inverts such a connection to achieve an aberration-free reconstructed image. Sample defocus is essentially equivalent to introducing a defocus phase factor to the pupil plane (i.e., a defocus aberration):

$$e^{i\cdot\varphi(k_x,k_y)} = e^{i\sqrt{(2\pi/\lambda)^2 - k_x^2 - k_y^2}\cdot z_0}, \quad k_x^2 + k_y^2 < (NA\cdot 2\pi/\lambda)^2 \quad \text{(Equation 2)}$$

where $k_x$ and $k_y$ are the wavenumbers at the pupil plane, $z_0$ is the defocus distance, and NA is the numerical aperture of the first objective.

In some implementations, the FP reconstruction process 800 begins in operation 801 with initializing a high-resolution image solution $\sqrt{I_h}e^{i\varphi_h}$ in the spatial domain. A Fourier transform is applied to obtain an initialized Fourier transformed image $\tilde{I}_h$. In some implementations, the initial high-resolution solution is determined based on the assumption that the sample is located at an out-of-focus plane $z=z_0$. In some other implementations, the initial solution is determined using a random complex matrix (for both intensity and phase). In some implementations, the initial solution is determined using an interpolation of the low-resolution intensity measurement with a random phase. In some implementations, an example of an initial solution uses $\varphi=0$ and uses $I_h$ interpolated from any low-resolution image of the sample area. In some implementations, an example of an initial solution uses a constant value. Regardless, the Fourier transform of the initial solution can be a broad spectrum in the Fourier domain.

In the iterative operations of 805, 810, 830, 845, 850, 860, and 870, the high-resolution image of the sample is computationally reconstructed by iteratively combining low-resolution intensity measurements in Fourier space.

In operation 805, the processor multiplies by a phase factor $e^{i\cdot\phi(k_x,k_y)}$ in Fourier domain. In operation 810, the processor performs low-pass filtering of the high-resolution image $\sqrt{I_h}e^{i\phi_h}$ in the Fourier domain to generate a low-resolution image $\sqrt{I_l}e^{i\phi_l}$ for a particular plane wave incidence angle $(\theta_x^i, \theta_y^i)$ with a wave vector $(k_x^i, k_y^i)$. The Fourier transform of the high-resolution image is $\tilde{I}_h$ and the Fourier transform of the low-resolution image for a particular plane wave incidence angle is $\tilde{I}_l$. In the Fourier domain, the process filters a low-pass region from the spectrum $\tilde{I}_h$ of the high-resolution image $\sqrt{I_h}e^{i\phi_h}$. This region is a circular aperture with a radius of $NA*k_0$, where $k_0$ equals $2\pi/\lambda$ (the wave number in vacuum), given by the coherent transfer function of the first objective lens. In Fourier space, the location of the region corresponds to the incidence angle. For an oblique plane wave incidence with a wave vector $(k_x^i, k_y^i)$, the region is centered about a position $(-k_x^i, -k_y^i)$ in the Fourier domain of $\sqrt{I_h}e^{i\phi_h}$.

In operation 830, using the processor, the computed amplitude component $\sqrt{I_{lf}}$ of the low-resolution image at the in-focus plane, $\sqrt{I_{lf}}e^{i\phi_{lf}}$, is replaced with the square root of the low-resolution intensity measurement $\sqrt{I_{lfm}}$ measured by the light detector of the IRI system. This forms an updated low resolution target: $\sqrt{I_{lfm}}e^{i\phi_{lf}}$. In operation 845, the processor multiplies by an inverse phase factor $e^{-i\cdot\phi(k_x,k_y)}$ in Fourier domain. At operation 850, a Fourier transform is applied to the updated target image propagated to the sample plane: $\sqrt{I_{ls}}e^{i\phi_{ls}}$, and this data is updated in the corresponding region of high-resolution solution $\sqrt{I_h}e^{i\phi_h}$ in the Fourier space corresponding to the corresponding to the incidence wave vector $(k_x^i, k_y^i)$. In operation 860, the processor determines whether operations 805 through 850 have been completed for all n uniquely illuminated low resolution intensity images. If operations 805 through 850 have not been completed for all for all n uniquely illuminated low resolution intensity images, operations 805 through 850 are repeated for the next image.

In operation 870, the processor determines whether the high-resolution solution has converged. In one example, the processor determines whether the high-resolution solution has converged to a self-consistent solution. In one case, the processor compares the previous high-resolution solution of the previous iteration or initial guess to the present high-resolution solution, and if the difference is less than a certain value, the solution has converged to a self-consistent solution. If processor determines that the solution has not converged, then operations 805 through 870 are repeated. In one embodiment, operations 805 through 870 are repeated once. In other embodiments, operations 805 through 870 are repeated twice or more. If the solution has converged, the processor transforms the converged solution in Fourier space to the spatial domain to recover the high-resolution image $\sqrt{I_h}e^{i\phi_h}$ and the FP reconstruction process ends.

Additional details of example FP reconstruction processes can be found in Zheng, Guoan, Horstmeyer, Roarke, and Yang, Changhuei, "Wide-field, high-resolution Fourier ptychographic microscopy," Nature Photonics vol. 7, pp. 739-745 (2013) and in U.S. patent application Ser. No. 14/065, 280, titled "Fourier Ptychographic Imaging Systems, Devices, and Methods" and filed on Oct. 28, 2013, both of which are hereby incorporated by reference herein in their entireties and for all purposes.

Figure 9:
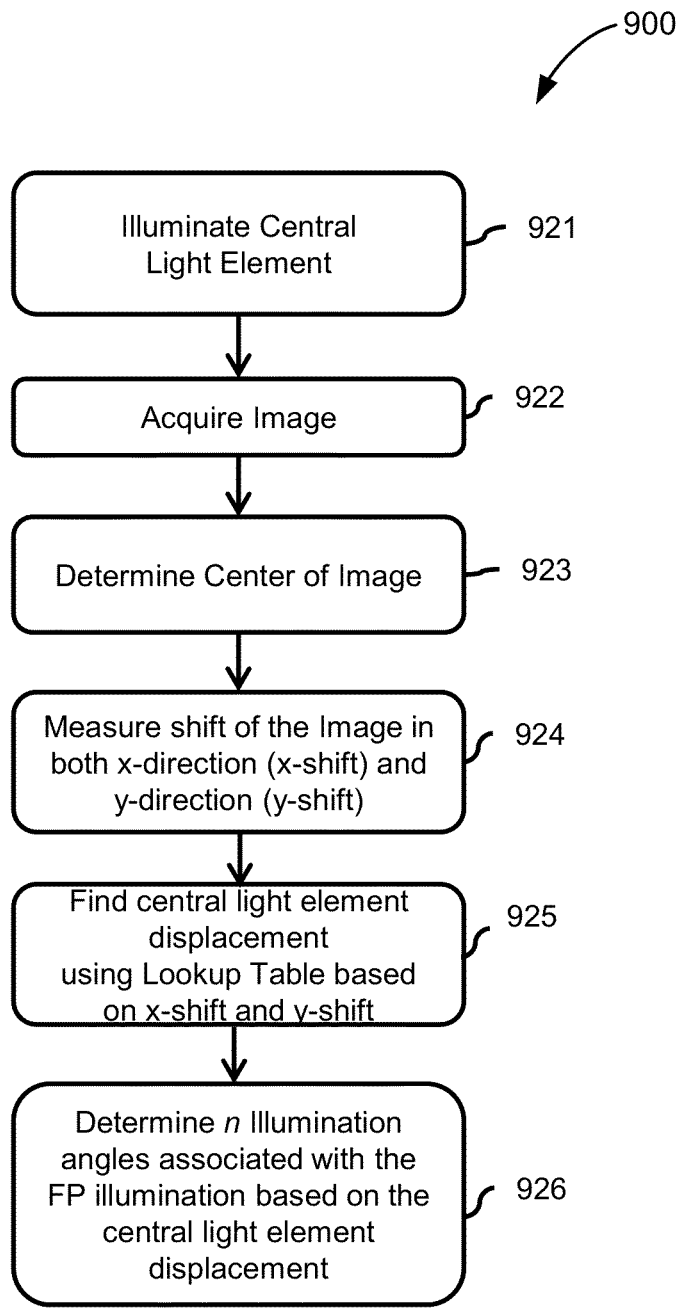
FIG. 9 shows a flowchart depicting operations of an example calibration process for determining the angles of incidence for each of the wells of a multi-well plate.

FIG. 9 shows a flowchart depicting operations of an example calibration process 900 for determining the angles of incidence for each of the wells of a multi-well plate. For example, the calibration process 900 can be performed during the initialization process in block 504 of the process 500 described with reference to FIG. 5. In block 921, the controller causes the illumination system to illuminate a central light element (for example, a respective one of the light sources 322) corresponding to at least one of the wells selected for the calibration process 900, and in some implementations, a plurality or even all of the wells. In some implementations, for example, the controller causes the illumination system to illuminate a central light element for only those wells in the four corners of the multi-well plate or only those wells in one or more particular columns and particular rows. In one embodiment, the controller determines the central light element by turning on light elements sequentially and capturing an image for each light element illumination. The central light element is determined based on the highest intensity image captured during the illumination by the multiple light elements.

In block 922, the controller causes each of the respective image sensors selected for the calibration process 900 to capture a vignette monochromic image during illumination by the central light element. In some implementations, the image is then converted to black and white. If there is a misalignment between the light element and the image sensor, the center of the image is shifted from the center of the image sensor. In block 923, the center of the image is determined. In block 924, the shift of the center of the image is measured along an x-axis direction (x-shift) and along a y-axis direction (y-shift). At operation 925, the displacement of the central light element is determined based on the x-shift and y-shift of the image using a lookup table or plot. The lookup table/plot provides different displacements of the central light element associated with different values of x-shift and y-shift. Once the displacement of the central light element is determined from the lookup table/plot, the illumination angles associated with the light elements in the variable illumination source can be determined based on the geometry of the variable illumination source. In block 926, precise values of the n illumination angles associated with the FP illumination are determined using the displacement of the central light element.

Figure 10A:
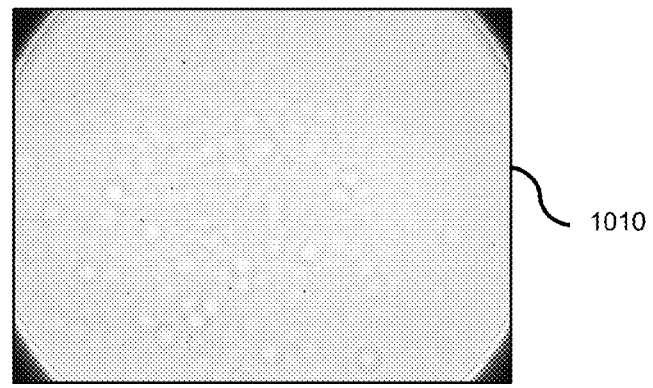
FIG. 10A shows a vignette monochromic image captured during illumination by a central LED of an LED matrix according to one example.
Figure 10B:
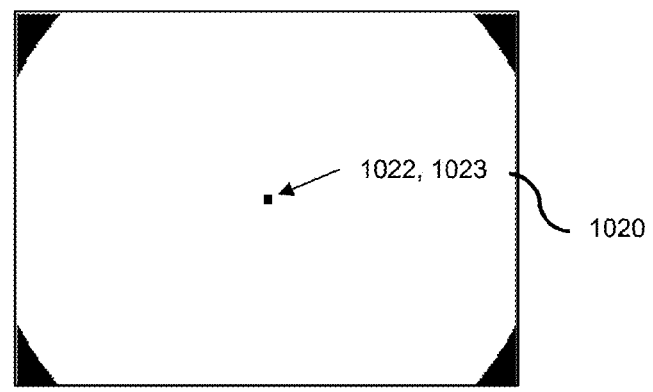
FIG. 10B is a converted black and white version of the color image of FIG. 10A.
Figure 10C:
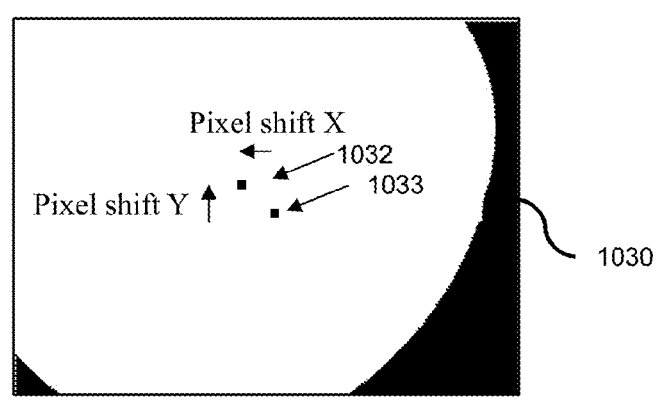
FIG. 10C shows an image captured during illumination by a center LED of a color LED matrix according to another example.
Figure 11:
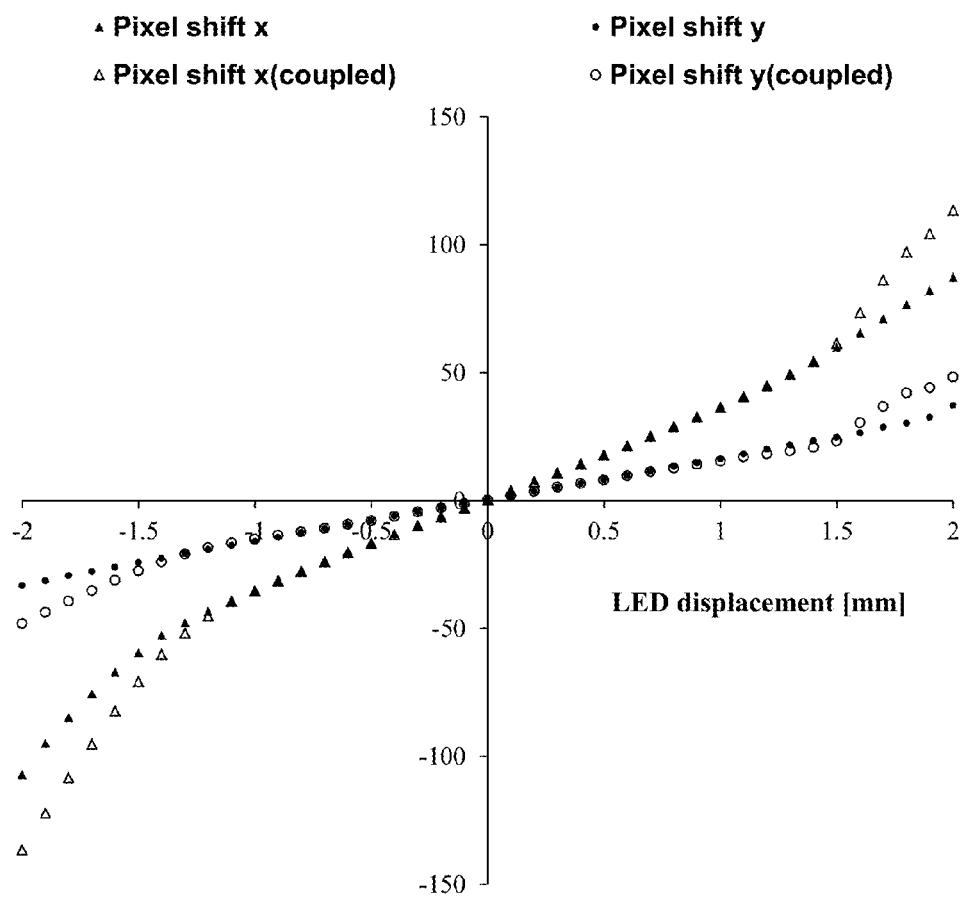
FIG. 11 shows a lookup plot of LED displacement associated with x-shift and y-shift of the center of the image with respect to the center of the image sensor, according to an embodiment.

FIG. 10A shows a vignette monochromic image captured during illumination by a central LED of an LED matrix according to one example. FIG. 10B is a converted black and white version of the image of FIG. 10A. In this example, the center 1022 of the black and white image is located at the same location as the center 1023 of the image sensor and the LED position is well aligned with the imaging sensor of the CMOS camera. FIG. 10C shows an image captured during illumination by a center LED of an LED matrix according to another example. In the example shown in FIG. 10C, there is a misalignment between the central LED and the image sensor. More specifically, there is a shift between the center 1032 of the image and the center 1023 of the image sensor. Even more specifically, there is a shift in the x direction (pixel shift X) and a shift in they direction (pixel shift Y). FIG. 11 shows a lookup plot of LED displacement associated with x-shift and y-shift of the center 1032 of the image with respect to the center 1023 of the image sensor, according to an embodiment. In this example, the lookup table was made by moving the LED matrix relative to the image sensor by known amounts and determining different shifts of the center of the image associated with the LED displacement.

Figure 12:
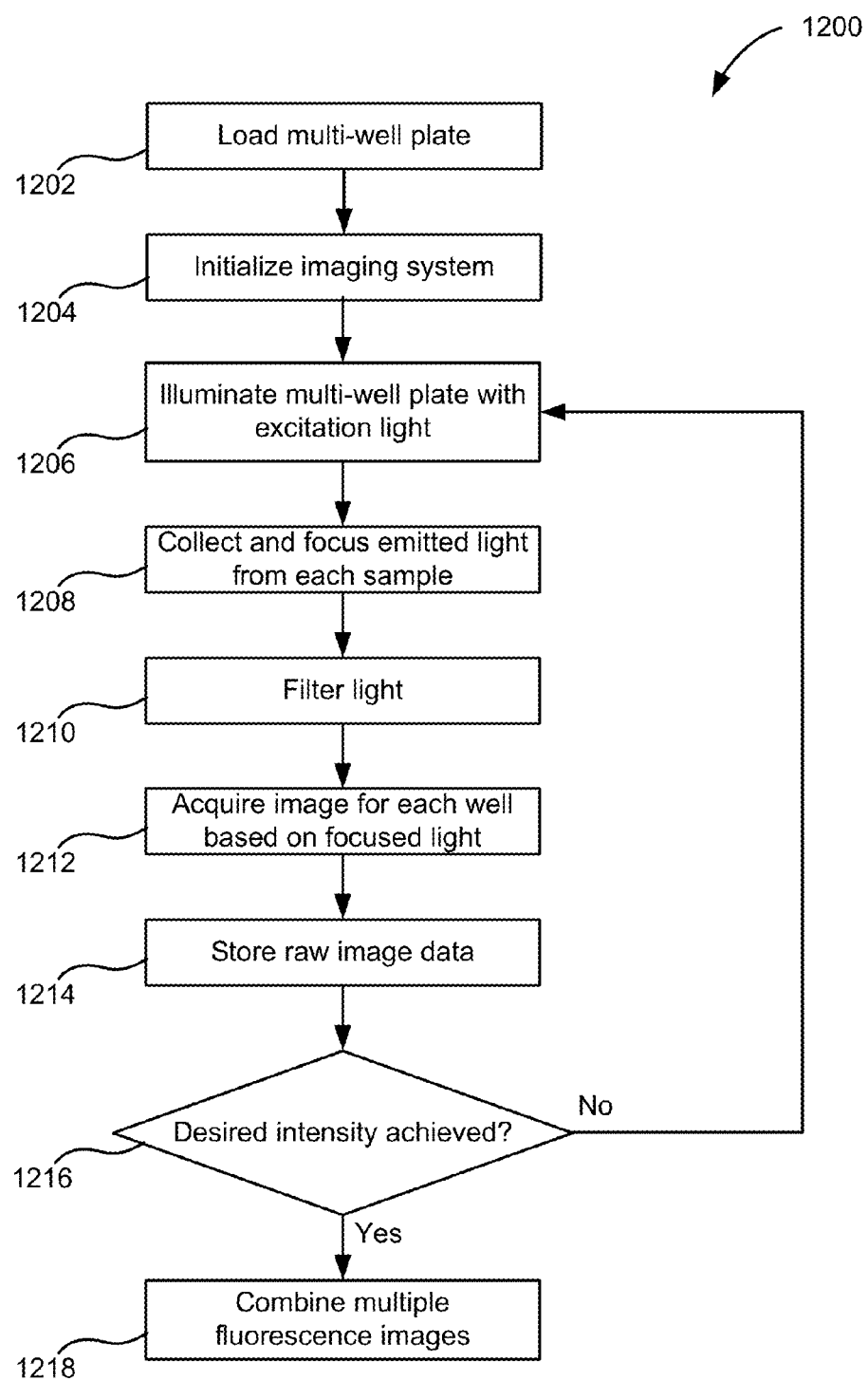
FIG. 12 shows a flowchart illustrating an example fluorescence imaging process 1200 for imaging a multi-well plate according to some implementations.

FIG. 12 shows a flowchart illustrating an example fluorescence imaging process 1200 for imaging a multi-well plate according to some implementations. For example, the process 1200 also can be performed using the systems, devices and arrangements described above with respect to FIGS. 1-4. In some implementations, the controller 110 is configured perform one or more operations of the fluorescence imaging process 1200. In some implementations, the fluorescence imaging process 1200 begins in operation 1202 with loading a multi-well plate into the imaging system. In some other implementations, the fluorescence imaging process 1200 can be performed automatically immediately (or shortly) after the FP imaging process 500 ends. In some other implementations, the fluorescence imaging process 1200 can begin between operations 502 and 506.

In operation 1204, the controller initializes the illumination system and the image sensor system. Initializing the illumination system in operation 1204 can include retrieving illumination information (such as the wavelength(s) of the excitation signals) from a non-volatile memory and loading the retrieved illumination information into a volatile memory for subsequent use in performing the imaging. Initializing the image sensor system in operation 1204 can include powering on or otherwise preparing the image sensors to receive light and to generate image data.

In operation 1206, the controller causes the illumination system to illuminate the multi-well plate with the excitation light. As described above, in operation 1206 all of the light sources 322 can be turned on simultaneously at a particular wavelength or within a particular range of wavelengths. Fluorophore in the sample are activated by the excitation light and emit light (emissions) of another range of wavelengths (e.g., blue, green or red light).

The lenses of the optical system receive (or "collect") light emitted by the respective samples and focus the received light onto the image sensors of the image sensor system. An optical filter filters the light such that only the light emitted by the fluorophore is propagated to the image sensors. Although the reception, focusing and filtering of the light is generally performed by passive elements (the lenses of the optical system and a color filter), this portion of the path of the light is still referred to as operation 1208 and 1210. In operation 1212, each of the image sensors receives light focused by a corresponding lens (or set of lenses) of the optical system and acquires fluorescence image data based on the focused light. In operation 1214, the image data may be stored in one or both of a volatile memory quickly accessible by a processor of the controller or a non-volatile memory for longer term storage. As described above, the image data represents an intensity distribution obtained during an exposure time.

In some implementations, in operation 1216, the processor determines whether a desired intensity has been achieved. If a desired intensity has not been achieved, operations 1206 through 1214 can be repeated multiple times and the resultant acquired fluorescence image data for each of the sample wells can be added or otherwise combined together in operation 1218 to obtain a desired intensity image for each of the sample wells.

In some implementations, for multi-band, multichannel embodiments, operations 1206 through 1214 can be repeated multiple times for each of multiple regions of the light spectrum (referred to as "bands"), and in some implementations, using different filters.

In some implementations, the controller generates a combined fluorescence and high resolution bright-field image of the sample by overlaying a fluorescence image generated by the fluorescence imaging process 1200 and a high resolution bright-field image generated by the FP imaging process 500. In another aspect, the processor generates a combined fluorescence and low resolution bright-field image of the sample by overlaying a fluorescence image generated by the fluorescence imaging process and a low resolution bright-field image captured during the acquisition process of the FP imaging process. In another aspect, the processor generates a high resolution phase image of the sample based on phase data in the FP imaging process.

In some implementations, the imaging systems described herein also can implement time-lapse imaging or other long term imaging. For example, the imaging processes 500 and 1200 can repeat at intervals such as, for example, one hour intervals, two hour intervals, one day intervals, etc. The imaging method can continue repeating each imaging run at intervals for a set period of time (e.g., one week, two weeks, one month, two months, etc.) or can run until an operator stops the imaging method. In some implementations, while this long term imaging continues, the imaging system can be located within an incubator.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Additionally, particular features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in particular combinations and even initially claimed as such, one or more features from a claimed combination can in some cases be excised from the combination, and the claimed combination may be directed to a subcombination or variation of a subcombination.

Similarly, while various operations (also referred to herein as "blocks") are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, the separation of various system components in the implementations described above should not be understood as requiring such separation in all implementations. Additionally, other implementations are within the scope of the following claims. In some cases, the actions recited in the claims can be performed in a different order and still achieve desirable results.

It will also be understood by persons having ordinary skill in the art that various functions, operations, processes, modules or components that described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

What is claimed is:

1. A Fourier ptychographic imaging system comprising:
an illumination system including an array of light sources;
a plate receiver system configured to receive a multi-well sample plate including an array of sample wells, and to align the multi-well sample plate with the array of light sources such that each sample well is capable of receiving light from a corresponding plurality of the light sources;
an optical system including at least one array of lenses, each lens configured to receive light from a corresponding sample well;
an imaging system including an array of image sensors, each image sensor configured to receive light from a corresponding lens and to acquire image data based on the received light; and
a controller configured to:
cause, for each scan of a plurality of scans, the illumination system to illuminate the array of sample wells in parallel and such that each of the sample wells is illuminated with light at an angle of incidence different than in the other scans of the plurality of scans;
cause, for each scan of the plurality of scans, the image sensors to acquire image data for the respective sample wells in parallel based on the illumination; and
perform a Fourier ptychographic operation to generate a reconstructed image for each of the sample wells based on the image data acquired for the respective sample well from the plurality of scans.

2. The imaging system of claim 1, wherein:
the plurality of scans includes n scans; and
the controller is configured to cause the illumination system to illuminate the array of sample wells such that each of the sample wells is illuminated with light at n different angles of incidence over the n respective scans.

3. The imaging system of claim 2, wherein the corresponding plurality of the light sources associated with each sample well includes n light sources, each of the n light sources being aligned with a different respective angle of incidence.

4. The imaging system of claim 1, wherein each of the sample wells is illuminated by one and only one light source during each scan.

5. The imaging system of claim 1, wherein each of the sample wells is illuminated by two or more light sources during at least one scan of the plurality of scans.

6. The imaging system of claim 1, wherein the plate receiver system is configured to align the multi-well plate between the illumination system and the optical system such that each of the sample wells is aligned with and between the corresponding plurality of the light sources and a corresponding set of one or more lenses of the at least one array of lenses.

7. The imaging system of claim 1, wherein the lenses of the at least one array of lenses are configured to focus light scattered by samples in the sample wells onto the respective image sensors.

8. The imaging system of claim 1, wherein the controller performs the Fourier ptychographic operation to generate the reconstructed images for the respective sample wells in parallel.

9. The imaging system of claim 1, wherein the Fourier ptychographic operation includes an aberration correction operation capable of correcting for aberrations.

10. The imaging system of claim 1, wherein the controller is further configured to:
cause the illumination system to illuminate the array of sample wells in parallel with excitation light configured to excite fluorophores;
cause the image sensors to acquire fluorescent image data for the respective sample wells in parallel based on light emitted by excited fluorophores in the array of sample wells; and
generate a fluorescent image for each of the sample wells in parallel based on the fluorescent image data acquired for the respective sample well.

11. The imaging system of claim 10, further comprising a filter configured to filter light at an excitation light wavelength and to pass light at an emitted light wavelength.

12. The imaging system of claim 1, wherein the controller is further configured to perform a calibration operation to determine values of the angles of incidence of the light that will illuminate each of the sample wells over the plurality of scans.

13. A method for performing Fourier ptychographic imaging comprising:
illuminating, by an array of light sources, for each scan of a plurality of scans, an array of sample wells in parallel and such that each of the sample wells is illuminated with light at an angle of incidence different than in the other scans of the plurality of scans;
acquiring, by an array of image sensors, for each scan of the plurality of scans, image data for the array of sample wells in parallel based on the illumination, wherein each image sensor is configured to receive light from a corresponding lens of an array of lenses and each lens is configured to receive light from a corresponding sample well; and
performing a Fourier ptychographic operation to generate a reconstructed image for each of the sample wells in parallel based on the image data acquired for the respective sample well from the plurality of scans, wherein the reconstructed image has higher resolution than the acquired image data.

14. The method of claim 13, wherein:
the plurality of scans includes n scans; and
each of the sample wells is illuminated with light at n different angles of incidence over the n respective scans.

15. The method of claim 14, wherein each of the sample wells is illuminated by n light sources over the plurality of scans, each of the n light sources being aligned with a different respective angle of incidence.

16. The method of claim 13, wherein each of the sample wells is illuminated by one and only one light source during each scan.

17. The method of claim 13, wherein each of the sample wells is illuminated by two or more light sources during at least one scan of the plurality of scans.

18. The method of claim 13, further comprising performing an aberration correction operation capable of correcting for aberrations.

19. The method of claim 13, further comprising:
   illuminating the array of sample wells in parallel with excitation light configured to excite fluorophores;
   acquiring fluorescent image data for the respective sample wells in parallel based on light emitted by excited fluorophores in the array of sample wells; and
   generating a fluorescent image for each of the sample wells in parallel based on the fluorescent image data acquired for the respective sample well.

20. The method of claim 13, further comprising performing a calibration operation to determine the values of the angles of incidence of the light that will illuminate each of the sample wells over the plurality of scans.

* * * * *